(12) United States Patent
You et al.

(10) Patent No.: US 7,772,230 B2
(45) Date of Patent: Aug. 10, 2010

(54) CHROMAN COMPOUND, PROCESSES FOR ITS PREPARATION, AND ITS PHARMACEUTICAL USE

(75) Inventors: Qidong You, Nanjing (CN); Lvpei Du, Nanjing (CN); Minyong Li, Nanjing (CN); Lin Xia, Nanjing (CN)

(73) Assignee: China Pharmaceutical University, Nanjing, Jiangsu (CN)

( * ) Notice: Subject to any disclaimer, the term of this patent is extended or adjusted under 35 U.S.C. 154(b) by 80 days.

(21) Appl. No.: 11/923,871

(22) Filed: Oct. 25, 2007

(65) Prior Publication Data

US 2008/0103307 A1 May 1, 2008

(30) Foreign Application Priority Data

Oct. 27, 2006 (CN) ......................... 2006 1 0097268

(51) Int. Cl.
*A61K 31/5377* (2006.01)
*A61K 31/496* (2006.01)
*A61K 31/454* (2006.01)
*A61K 31/4178* (2006.01)
*C07D 407/12* (2006.01)
*C07D 409/12* (2006.01)

(52) U.S. Cl. .............. 514/233.5; 514/254.07; 514/320; 514/324; 514/390; 544/139; 544/370; 546/196; 548/311.4

(58) Field of Classification Search ....................... None
See application file for complete search history.

*Primary Examiner*—Emily Bernhardt
(74) *Attorney, Agent, or Firm*—Global IP Services; Tianhua Gu

(57) ABSTRACT

The present invention provides a chroman compound of formula (I) and its pharmaceutical salt, methods of its preparation and its pharmaceutical applications. Wherein: X is O or S; n is for 2, 3 or 4; $R_1$ is 6-substituted or 7-substituted halogen, $C_{1-4}$alkyl, $C_{1-4}$alkoxyl, benzyloxy, carbamoyl; $R_2$ is nitrogen-containing five-membered or six-membered substituted heterocyclic ring selected from piperidinyl, morpholinyl, N-methyl-piperazinyl, N-(2-ethoxyl)piperazinyl, pyrrolyl, pyrazolyl or imidazolyl. The compounds are useful to prepare medicaments for treating cardiovascular diseases, their preparation employs mild reaction conditions, the raw material are plenty and easy to be obtained, and the operation and post-treatment in the preparation are simple.

(I)

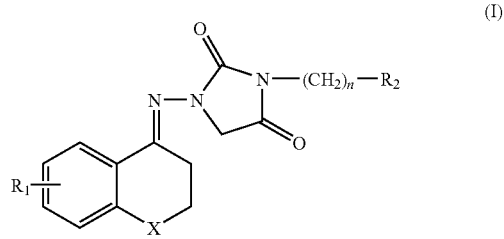

5 Claims, No Drawings

CHROMAN COMPOUND, PROCESSES FOR ITS PREPARATION, AND ITS PHARMACEUTICAL USE

FIELD OF THE INVENTION

The present invention belongs to pharmaceuticals synthesis field, it relates to a chroman compound. The present invention also relates to the method for preparing the compound and its pharmaceutical use.

PRIOR ART

According to the electrophysiological effect and its mechanism of drugs obtained from Purkinje fibre in vitro experiment, the anti-arrhythmic drugs are usually classed into four groups: I—sodium channel blockers; II—β-adrenoreceptor blockers; III—agents for selective prolonging repolarization; IV—calcium antagonists. From 1970s to the early 1980s of $20^{th}$ century, the developing strategy of anti-arrhythmic drug is based on inhibiting ventricle early contraction in the animal models or patients having PVCs after myocardial infarction. However, in recent decade, there are significant changes in treating arrhythmia by drugs. Due to the results of CAST experiment, the research focus has already switched from anti-arrhythmic drugs of group I to anti-arrhythmic drugs of group III, the studies on potassium ion channel blockers have been largely developed. Thereafter, the reported anti-arrhythmic drugs are almost potassium ion channel blockers which may be safer, have broader spectrum and more active compared with other types anti-THP-arrhythmic drugs, which are expected to be preferred anti-arrhythmic drugs.

The conventional class III anti-arrhythmic drugs usually block cardiac rapidly delayed rectifier potassium channel current ($I_{Kr}$). There are two disadvantages: leading to cardiac side effects and stimulating β-receptor. It should be considered that due to the QT wave extends after the $I_{Kr}$ is blocked, which consequently result in slowly activating the acutely elevated response of the potassium channel current ($I_{Ks}$).

In order to avoid these disadvantages, many pharmaceutical companies and institutes are engaged in developing such anti-arrhythmia drugs enabling blocking the $I_{Ks}$ of cardiac muscle. The anti-arrhythmia drugs having $I_{Kr}$ and $I_{Ks}$ double blocking influence are better than selective $I_{Kr}$ blockades in anti-arrhythmia effect. Furthermore, they may reduce the arrhythmia side-effect. Therefore, class III anti-arrhythmic drugs with dual $I_{Kr}$ and $I_{Ks}$ blockade effect is the new hot point in developing anti-arrhythmic drugs at present.

SUMMARY OF INVENTION

The object of the present invention is to developing a chroman compound having dual blockade influences on both the rapidly delayed rectifier potassium channel current ($I_{Kr}$) and the slowly delayed rectifier potassium channel current ($I_{Ks}$) in cardiac myocytes.

Another object of the present invention is to provide the method for preparing the chroman compound above-mentioned.

Another object of the present invention is to provide the use of such chroman compound above-mentioned in the medicaments for treating cardiovascular diseases.

The objects of the present invention will be carried out by following technical steps:

A chroman compound, described as formula (I) or its pharmaceutical salts:

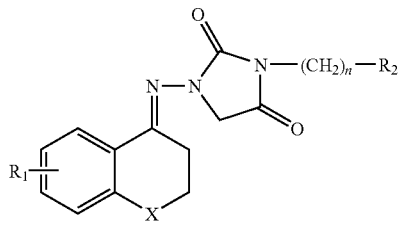

in which X is O or S; n is 2, 3, or 4; $R_1$ is 6-substituted or 7-substituted halogen, $C_{1-4}$alkyl, $C_{1-4}$alkoxyl, benzyloxyl, carbamoyl; $R_2$ is nitrogen-containing five-membered or six-membered substituted heterocyclic ring.

The said chroman compound wherein $R_2$ is piperidinyl, morpholinyl, N-methyl-piperazinyl, N-(2-ethoxyl)piperazinyl, pyrrolyl, pyrazolyl or imidazolyl.

The pharmaceutical salt of the said chroman compound refers to the difumarate thereof.

A method for preparing the said chroman compound comprises the following steps:

(1) $R_1$ substituted phenol is used as the starting material, reacting with 3-chloropropionic acid in the presence of KOH or NaOH to obtain intermediate compound 3-($R_1$ substituted phenoxyl)propionic acid;

(2) Dissolving the 3-($R_1$ substituted phenoxyl) propionic acid in polyphosphonic acid, stirring, to obtain intermediate compound 2,3-dihydro-6(7)-$R_1$ substituted benzopyran-4-one;

(3) Stirring the 2,3-dihydro-6(7)-$R_1$ substituted benzopyran-4-one in refluxing HBr and glacial acetic acid, to obtain 2,3-dihydro-6(7)-hydroxyl benzopyran-4-one;

(4) Reacting 2,3-dihydro-6(7)-hydroxyl benzopyran-4-one with haloalkyl or haloaryl hydrocarbons in the presence of $K_2CO_3$, $Na_2CO_3$, or $NaHCO_3$ and acetonitrile or acetone, stirring at refluxing to obtain intermediate compound 2,3-dihydro-6(7)-alkoxy-$R_1$ substituted benzopyran-4-one or 2,3-dihydro-6(7)-benzyloxy-$R_1$ substituted benzopyran-4-one;

(5) Reacting 2,3-dihydro-6(7)-substituted benzopyran-4-one with compound (III) in the solvent selected from methanol, ethanol or n-butyl alcohol, adjusting pH to the range of 3-6 by glacial acetic acid, stirring at refluxing to obtain target compound of formula (I); optionally subsequently reacting the target compound of formula (I) with fumaric acid to obtain the difumarate of the target compound;

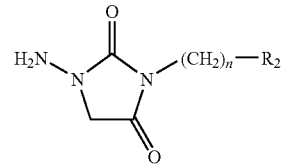

in which n is 2, 3 or 4; $R_1$ is 6-substituted or 7-substituted halogen, $C_{1-4}$alkyl, $C_{1-4}$alkoxyl, benzyloxyl, carbamoyl; $R_2$ is nitrogen-containing five-membered or six-membered substituted heterocyclic ring.

The compounds are useful to prepare medicaments for treating cardiovascular diseases.

The embodiments of the present invention will be described in more details as follows:

A compound of chroman, having the structure of formula (Ia):

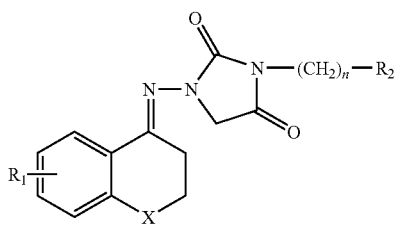

(Ia)

in which X is O or S; $R_1$ is 6-substituted or 7-substituted halogen F, Cl, or Br, or linear or branched alkyl having 1 to 4 carbon atoms or carbamoyl, $R_2$ is nitrogen-containing pentatomic or hexahydric heterocyclic ring; and n is 2, 3 or 4.

The synthesis process of formula (Ia) can be summarized as follow:

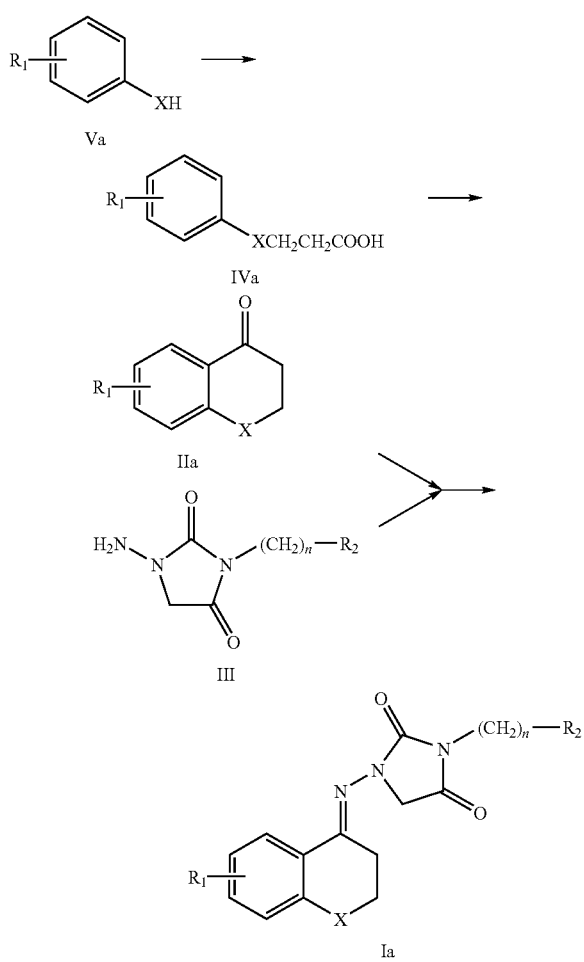

1. Preparation for the Compound of Formula (IVa):

Solid KOH and water are added to the compound (Va), which is stirred at room temperature, in the meanwhile 3-chloropropionic acid is added, then stirred and refluxed for 2 h, the resultant reaction solution is accommodated to pH 1-2 with concentrated hydrochloric acid, extracted with ether; and then the ether layers are combined, washed with 10% $NaHCO_3$ aqueous solution, followed by accommodating pH 3-4 with concentrated hydrochloric acid, and then the solid is precipitated. The resultant solid is filtered, and the filter cake is recrystallized by benzene to obtain crystals in the forms of white needle.

2. Preparation for the Compound of Formula (IIa):

Polyphosphonic acid is added the compound (IVa), which is heated and stirred for 1.5 h, and then debris ice is added. The resultant mixture is extracted with ethyl acetate, the organic layer is washed with saturated $NaHCO_3$ aqueous solution until neutral and dried with anhydrous $Na_2SO_4$, concentrated, refrigerated, and then crystals are precipitated. The resultant crystals are recrystallized by ethyl acetate or petroleum ether, decompressing dried at room temperature.

3. Preparation for the Compound of Formula (Ia):

Anhydrous methanol, ethanol or n-butanol and glacial acetic acid are added to the compound (IIa) and (III), the resultant mixture is stirred and refluxed. The pH of the mixture is then accommodated for almost neutral, and the mixture is extracted with chloroform, the organic layer is dried with anhydrous $Na_2SO_4$, and concentrated, followed by adding fumaric acid, the light yellow solid is precipitated. The residue is filtered and the filter cake is recrystallized by anhydrous ethanol or anhydrous methanol.

Optionally, the compounds having the structure of formula (Ib):

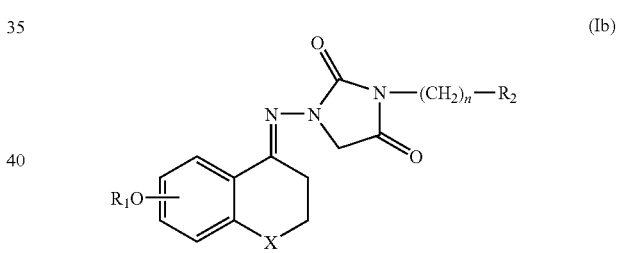

(Ib)

in which, X is O or S; $R_1$ is saturated linear or branched alkyl having 1 to 4 carbon atoms or aryl; $R_2$ is nitrogen-containing six-membered or five-membered substituted heterocyclic ring;

n is 2, 3, or 4.

The preparation of the compound of formula (Ib) can be summarized as follow:

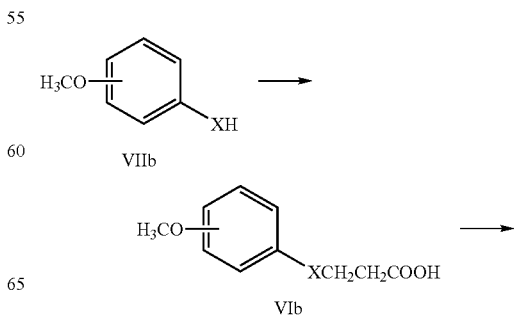

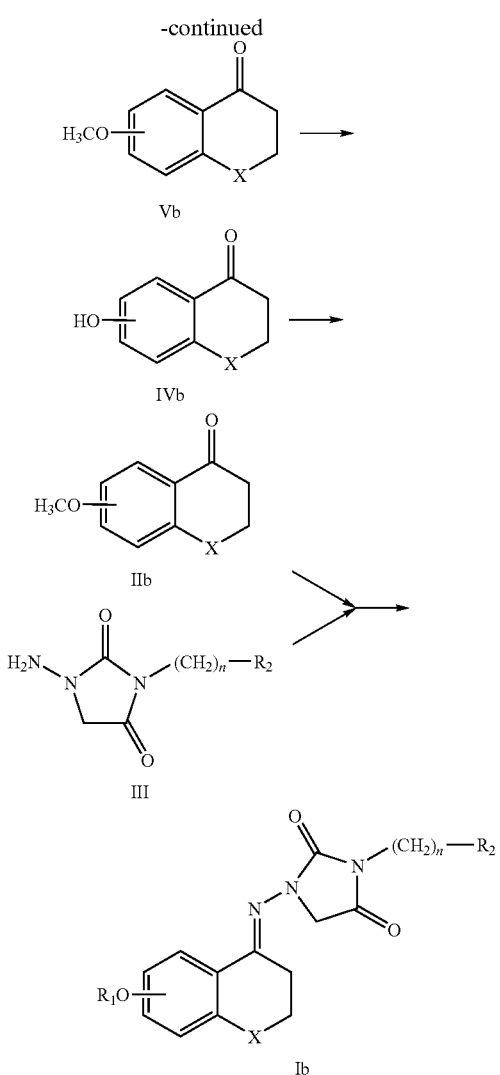

1. The Preparation of the Compound of Formula (VIb):

Solid KOH and water are added to the compound (VIIb), which is stirred at room temperature, in the meanwhile 3-chloropropionic acid is added, then the mixture is stirred and refluxed for 2 h, the resultant reaction solution is accommodated to pH 2 with concentrated hydrochloric acid, extracted with ether; and then the ether layers are combined, washed with 10% NaHCO$_3$ aqueous solution, followed by accommodating to pH 3-4 with concentrated hydrochloric acid, and then the solid is precipitated. The residue is filtered, and the filter cake is recrystallized by benzene to obtain crystals in the forms of white needle.

2. Preparation for the Compound of Formula (Vb):

Polyphosphonic acid is added to the compound (VIb), which is heated and stirred, and then debris ice is added. The resultant mixture is extracted with ethyl acetate, the organic layer is washed with 10% NaHCO$_3$ aqueous solution until neutral and dried with anhydrous Na$_2$SO$_4$, concentrated, refrigerated, and then white crystals precipitate. The resultant crystals are recrystallized by ethyl acetate, decompressing dried at room temperature to obtain the crystals in the forms of white needle.

3. Preparation for the Compound of Formula (IVb):

Glacial acetic acid and HBr (the concentration of hydrobromic acid is more than 40% by weight) are added to the compound (Vb) orderly. After the resultant reaction solution is concentrated, the mixture is then accommodated pH 10-11 with KOH, and the mixture is further accommodated pH 2-3 with concentrated hydrochloric acid. The resultant mixture is extracted by ethyl acetate. The organic layers are combined and dried with anhydrous Na$_2$SO$_4$, then concentrated and refrigerated, the solid is precipitated. The residue is filtered and the solid is recrystallized by ethyl acetate, dried under the infrared lamp to obtain bright yellow crystals.

4. Preparation the Compound of Formula (IIb):

Haloalkyl or haloaryl hydrocarbon, and K$_2$CO$_3$, Na$_2$CO$_3$ or NaHCO$_3$ and acetone are added to compound (IVb), the resultant mixture is stirred and refluxed, then washed with 10% KOH aqueous solution. The organic layer is dried with anhydrous Na$_2$SO$_4$, and then concentrated to obtain brown oil. The oil is refrigerated to precipitate white needle like crystals. The residue is filtered and recrystallized from petroleum ether, dried under the infrared lamp.

5. Preparation for the Compound of Formula (Ib):

Anhydrous ethanol (or anhydrous methanol, n-butanol) and glacial acetic acid are added to the compound (IIb) and (III), the resultant mixture is stirred and refluxed. The pH of the mixture is then accommodated for almost neutral with NaOH, and the mixture is extracted with chloroform, the organic layer is dried with anhydrous Na$_2$SO$_4$, and concentrated, followed by adding fumaric acid, the light yellow solid precipitate. The residue is filtered and the solid is recrystallized from anhydrous ethanol.

The beneficial effect of the present invention:

The chroman compounds provided according to the present invention have strong anti-arrthhythmia activity, which can be used to prepare anti-arrthythmia drugs. The method for preparing such chroman compounds provided in the present invention has some advantages as which their preparation employs mild reaction conditions, the materials are enrich and easily to obtained, and the process and post treatment in the preparation are simple and so on.

1. The Determination of Biological Activity:

Experimental title: using vitro pachynsis myocardial cells of Guinea pig, the activity is determined by the whole cell membrane Patch clamp technology.

experimental mechanism: the Guinea pig myocardial cells are separated with enzymolysis, and the rapid activation component and the slowly activation component of the delayed commutating current in the cardiac muscle cells are recorded by whole cell membrane Patch clamp. Each compound is added to the perfuse liquid for measuring current after dissolved at least 10 min. The collected data is analyzed in pulse-fit, the IC$_{50}$ value for I$_{Kr}$ and I$_{Ks}$ of each compound is calculated.

1. Materials and Methods:

animals: Guinea pigs, male, weight 300-400 g.
solution: calcium free Tyrode's solution
pole inner solution (mmol/L): KCl 140, MgCl$_2$ 1.0, K$_2$-ATP 4.0, EGTA 10, HEPES 5.0, pH=7.2

Experimental apparatus: Patch clamp magnifier (EPC-10, Germany), inverted microscope (TE-2000U, Nikon, Japan), microelectrode puller (PIP5, Germany), micro-manipulator (PCS-5000, Burleigh, USA).

Experiment:

the separation of the Guinea pig myocardial cell: the Guinea pigs are stunned and their hearts are taken out and then put into the calcium free Tyrode's solution, then these hearts are laid on the langendorff device after being cropped, such hearts are perfused with calcium free Tyrode's solution for 5 min, and then perfused with low calcium Tyrode's solution containing type II collagenase 1 mg/mL, protease 0.1 mg/mL, BSA 0.5% and $CaCl_2$ 150 μmol/L until the hearts become soft and relaxed. Then, the hearts are taken off, their ventricle are cut to smash and incubated in fresh enzyme solution at 37° C., the solution is gently stirred for 5-10 min, pouring off the supernatant fluid, diluted with Tyrode's solution containing $CaCl_2$ 1 mmol/L, that is for the first cell stored liquor; with the same operation to obtain the second and the third cell storages. The perfused solution is saturated with 5% $CO_2$+95% $O_2$. The cells are laid for 2 h before use.

2. Whole Cell Patch Clamp Technique:

the cell liquor is put into the cell pool, after the cells adhering to the wall, they are perfused with outer liquor of the cells at the rate of 2 ml/min, cells that having calcium resistance and clear transverse striations are to be selected, the poles are moved to the cell surface by tridimensional manipulator. The high resistance block are formed between the pole top and the cell surface by under pressure, and more over using reduced pressure to broking cell membrane, the pole inner liquor can be connected to the cell inner liquor so as to form the whole cell state. After the compensation to the capacitance and series impedance compensation the voltage tongs are recorded. The signal is led by Ag/AgCl pole and magnified by the Patch clamp magnifier, the computer dispenses presetting stimulate pulse by procedure and add to cells, and the electrical signal generated from cells is translated by transducer, and stored in computer. All of the stimulate signal control, electric current, data sampling and analyses are carried out by pulse V8.60. Azimilide is used as positive drugs in the research. Each test compound is dissolved in anhydrous ethanol, diluted to the same concentration by water, and added to outer cell liquor, the top concentration of ethanol is 0.1%. The pre-experiment result has showed that such concentration would not affect the experiment results. The drugs are administrated after the recording current has been stabilized 10 min, 10 min after the administration, the current are recorded, this experiment is proceed at 25-30° C.

Stimulate parameter: the record of $I_{Kr}$ and $I_{Ks}$: the back value of the either current is recorded. Using extra-cellular fluid containing 0.1 mmol/L $CdCl_2$ for perfusion, sustaining the voltage at −50 mV, depolarized to 60 mV, keeping for 500 ms, and sustaining the voltage at −50 mV, keeping for 1000 ms, recording $I_{Kr}$; and then binding the voltage at −50 mV for 1000 ms, recording $I_{Ks}$.

Results:

| compound | $I_{Kr}IC_{50}$ (μM) | $I_{Ks} IC_{50}$ (μM) |
|---|---|---|
| Ia example 1 | 1.01 | 0.65 |
| Ia example 2 | 4.7 | 0.073 |
| Ia example 4 | 0.45 | 0.33 |
| Ia example 5 | 7.47 | 22 |
| Ia example 6 | 0.0062 | 61 |
| Ia example 7 | 22 | 18.9 |
| Ia example 8 | 0.54 | 0.0019 |
| Ia example 9 | 0.619 | 0.304 |
| Ia example 10 | 3.87 | 0.0058 |
| Ib example 3 | 11.8 | 1.28 |
| Ib example 4 | 0.18 | 0.022 |
| Ib example 5 | 0.45 | 1.04 |
| Ib example 6 | 0.4 | 0.0032 |
| Ib example 7 | 0.0174 | 1.03 |
| Ib example 9 | 4.34 | 0.0269 |

-continued

| compound | $I_{Kr}IC_{50}$ (μM) | $I_{Ks} IC_{50}$ (μM) |
|---|---|---|
| Ib example 10 | 0.106 | 0.0095 |
| Ib example 11 | 39.7 | 1.23 |
| Positive drug | 0.18 | 0.24 |

As shown in the result, the chroman compounds have strong anti-arrhythmia activity, which will be used as anti-arrhythmia drugs.

EMBODIMENTS

The present invention will be further described in more details below by examples which are not limited to the present invention.

General Explanation:

Melting point is measured by XT-4 type binocular micro melting point instrument (Manufactured by Peking Tek Instrument limited company). IR spectra is mensurated by Nicolet Impact 410 type Fourier Transform infrared spectrometry instrument, KBr tabletting. Elemental analysis is measured by Elementar Vario EL III type elemental analysis instrument.

$^1$H-NMR spectra is measured by Bruker AMX-300. ACF-300, ACF-500 type nuclear magnetic resonance apparatus, TMS is used as internal standard. MS spectra is measured by Agilent 6890 GC/MS and Agilent 1100 Series LC/MSD type mass spectroscope. Thin-layer chromatography (TLC) Board is prepared by triturating silica gel GF254 (QingDao ocean chemistry factory) and 8% CMC-Na of distilled water completely and then paving, which is activated at the temperature of 100-120° C. for 1 h to get ready for use, developed under the uviol lamp (3650 Å) or iodine. Column chromatography using 100-200 mesh silica gel (produced by QingDao ocean chemistry factory), wet method packing; all of the reagent are commercial source and chemically pure or analytically pure product, unless the special mentions, these are directly used without treating.

EXAMPLES FOR COMPOUND OF FORMULA
(Ia)

Example 1

1-[4-(2,3-dihydro-6-methoxy)benzopyran]imino-3-[4-(methyl-1-piperazine) butyl]-2,4-imidazole dione difumarate

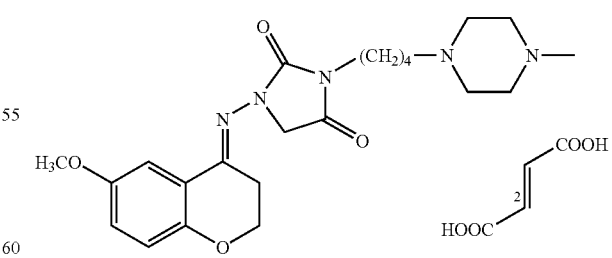

(1) Preparation of 3-(4-methoxyphenoxy)propanoic acid

Solid KOH (6.80 g, 0.122 mol) and $H_2O$ (10 mL) are added to 4-methoxyphenol (7.0 g, 0.0564 mol), the resultant mixture is stirred at the room temperature while 3-chloropropanoic acid (6.12 g, 0.0564 mol) is added to thereof. Then the mixture is stirred and heated to reflux for 3 h. The mixture is acidified to pH 2 by adding concentrated aqueous HCl and extracted with ether. The combined ether extracts is then washed by 10% aqueous NaHCO₃ and acidified to pH 3-4 by adding concentrated aqueous HCl, and precipitate was formed. The residue is filtered and recrystallized by benzene to provide needle crystal 2.0 g. m.p.: 102-103° C., yield: 18.1%.

(2) Preparation of 2,3-dihydro-6-methoxy-benzopyran-4-one

Polyphosphonic acid (45 mL) is added to 3-(4-methoxyphenoxyl)propanoic acid (2.0 g, 0.010 mol). The mixture is stirred and heated for 2 h. To the mixture, 15 g debris ice is added. The reaction mixture was extracted by ethyl acetate and the combined ethyl acetate extracts are washed with 10% aqueous NaHCO₃ to neutral, dried over Na₂SO₄, concentrated and cooled to provide crystal, which is recrystallized from ethyl acetate to provide white needle crystal 1.63 g. m.p.: 44-45° C., yield: 91.6%.

(3) Preparation of Title Compound

Anhydrous n-butanol 10 mL and glacial acetic acid are added to 1-amino-3-[4-(4-methyl-1-piperazine) butyl]-2,4-imidazole dione, and then the solution of 2,3-dihydro-6-methoxybenzopyran-4-one 0.56 g (0.00316 mol) in 10 mL n-butanol is dropped. The mixture is heated to reflux for 10 h, and then modulated the pH for 7 with NaOH, extracted with chloroform. The organic layer was dried over Na₂SO₄, concentrated and treated with fumaric acid to form precipitate. The residue is filtered and recrystallized by ethanol to provide light yellow solid 0.34 g, m.p.: 208-210° C., yield: 19.77%.

IR (KBr, cm⁻¹): 3470, 2941, 2425, 1708, 1492, 759, 753;
ESI-MS: [M+H]⁺: 430.2;
¹H-NMR (DMSO-d6), δ: 11-14 (w, 4H, 4-COOH), 7.38 (d, 1H, Ar—H), 7.02 (dd, 1H, Ar—H), 6.90 (d, 1H, Ar—H), 6.59 (s, 4H, 4×HOOC—CH═), 4.36 (s, 2H,

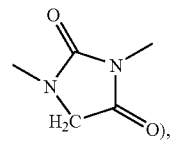

), 4.20 (t, 2H,

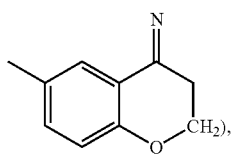

), 3.72 (s, 3H, —OCH3), 3.43 (t, 2H,

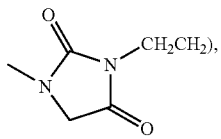

), 2.89 (t, 2H,

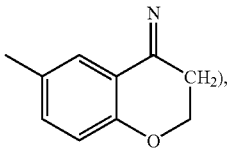

), 2.50 (s, 8H,

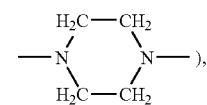

), 2.34 (t, 2H,

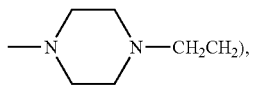

), 2.29 (s, 3H,

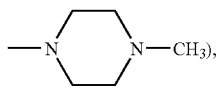

), 1.56 (m, 2H,

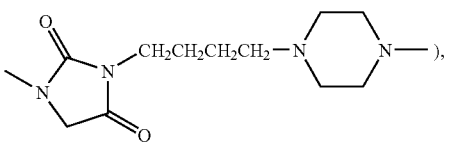

), 1.43 (m, 2H,

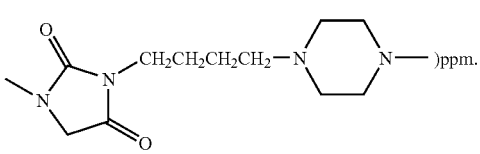

)ppm.

Example 2

1-[4-(2,3-dihydro-6-chloro) benzopyran]imino-3-[4-(methyl-1-piperazine) butyl]-2,4-imidazole dione difumarate

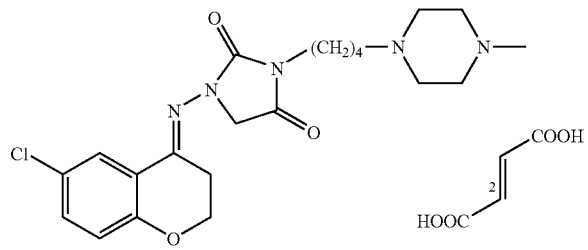

processing as the step (1) in the method of example 1, except for parachlorophenol in place of para-hydroxybenzene methyl ether, to obtain 3-[4-chlorophenoxy]propionic acid, m.p.: 135-136° C., yield: 22.58%.

processing as the step (2) in the method of example 1, using 3-[4-chlorophenoxy]propionic acid as starting material, to obtain 2,3-dihydro-6-chloro benzopyran-4-one in the forms of yellow needle crystal 3.65 g, m.p.: 100-102° C., yield: 98.6%.

processing as the step (3) in the method of example 1, 2,3-dihydro-6-chloro benzopyran-4-one is reacted with 1-amino-3-[4-(4-methyl-1-piperazine) butyl]-2,4-imidazole dione, to obtain the title compound in the forms of white powder 0.43 g, m.p.: 230-232° C., yield: 46.08%.

IR (KBr, cm$^{-1}$): 3420, 2389, 2955, 1712, 1417, 1309, 979, 763, 639;

ESI-MS: [M+H]$^+$: 434.2 (isotopic peak: 436.1);

$^1$H-NMR (DMSO-d6): δ 10.5-14.5 (w, 4H, 4-COOH), 7.86 (s, 1H, Ar—H), 7.45 (dd, 1H, Ar—H), 7.43 (d, 1H, Ar—H), 6.58 (s, 4H, 4×HOOC—CH=), 4.39 (s, 2H

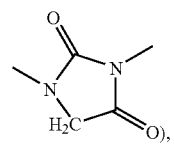

4.28 (t, 2H,

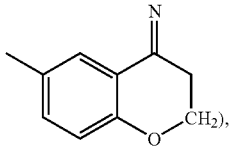

3.43 (t, 2H

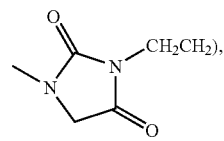

2.90 (t, 2H,

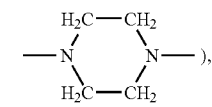

2.50-2.58 (m, 5H,

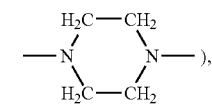

2.49 (s, 3H,

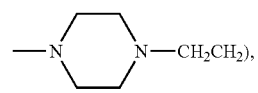

2.38 (t, 2H,

—N\_/N—CH$_2$CH$_2$), 2.32 (s, 3H,

—N\_/N—CH$_3$), 1.55 (m, 2H,

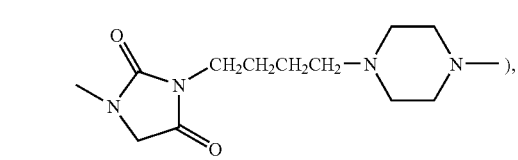

1.44 (m, 2H,

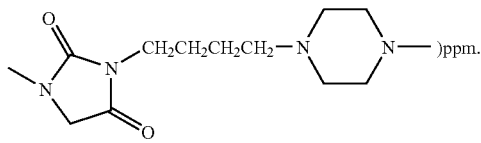
)ppm.

Example 3

1-[4-(2,3-dihydro-6-methyl)benzopyran]imino-3-[4-(methyl-1-piperazine) butyl]-2,4-imidazole dione difumarate

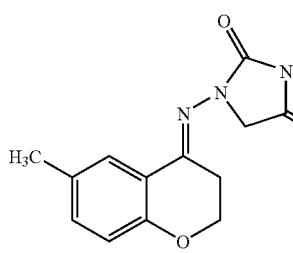 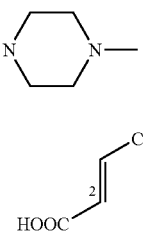

processing as the step (1) in the method of example 1, except for para-methylphenol in place of para-hydroxybenzene methyl ether, to obtain 3-[4-methylphenoxy]propionic acid, m.p.: 145-147° C., yield: 10.9%.

processing as the step (2) in the method of example 1, using 3-[4-methylphenoxy]propionic acid as starting material, to obtain 2,3-dihydro-6-methyl benzopyran-4-one in the forms of yellow needle crystal 3.65 g, m.p.: 100-102° C., yield: 98.6%.

processing as the step (3) in the method of example 1, 2,3-dihydro-6-methyl benzopyran-4-one is reacted with 1-amino-3-[4-(4-methyl-1-piperazine) butyl]-2,4-imidazole dione, to obtain the title compound in the forms of white powder 0.43 g, m.p.: 231-233° C., yield: 59.0%.

IR (KBr, cm$^{-1}$): 2948, 1719, 1298, 978, 762, 637;

ESI-MS: [M+H]$^+$: 414.2; [M+Na]$^+$: 436.2;

$^1$H-NMR (DMSO-d6): δ 10.5-14.5 (w, 4H, 4-COOH), 7.72 (s, 1H, Ar—H), 7.23 (dd, 1H, Ar—H), 6.84 (d, 1H, Ar—H), 6.58 (s, 4H, 4×HOOC—CH═), 4.35 (s, 2H,

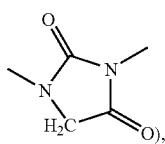
), 4.21 (t, 2H,

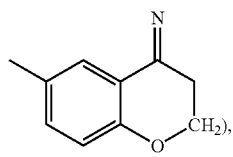
), 3.43 (t, 2H,

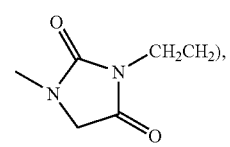
), 2.87 (t, 2H,

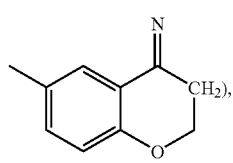
), 2.52 (s, 4H

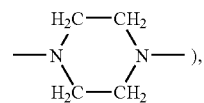
), 2.49 (s, 4H,

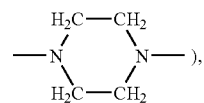
), 2.37 (t, 2H,

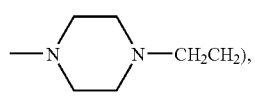
), 2.33 (s, 3H,

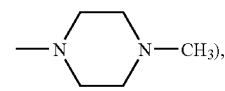
), 1.55 (m, 2H,

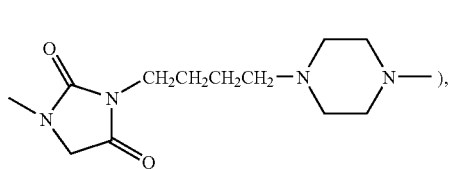

1.44 (m, 2H,

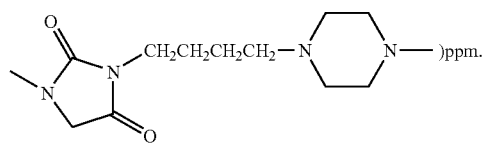)ppm.

Example 4

1-[4-(2,3-dihydro-6-carbamoyl)benzopyran]imino-3-[4-(methyl-1-piperazine) butyl]-2,4-imidazole dione difumarate

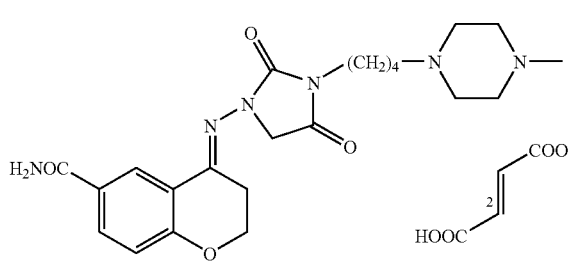

processing as the step (1) in the method of example 1, except for para-carbamoylphenol in place of para-hydroxybenzene methyl ether, to obtain 3-[4-nitrilephenoxy]propionic acid, m.p.: 147-149° C., yield: 29.32%.

Processing as the step (2) in the method of example 1, using 3-[4-nitrilephenoxy]propionic acid as starting material, to obtain 6-carbamoyl-2,3-dihydro-4H-1-benzopyran-4-one in the forms of light yellow sheet crystal 3.65 g, m.p.: 228-229° C., yield: 71.73%.

processing as the step (3) in the method of example 1,6-carbamoyl-2,3-dihydro-4H-1-benzopyran-4-one is reacted with 1-amino-3-[4-(4-methyl-1-piperazine) butyl]-2,4-imidazole dione, to obtain the title compound in the forms of white powder 0.20 g, m.p.: 192-194° C., yield: 16.26%.

IR (KBr, cm$^{-1}$): 3473, 2949, 2422, 1705, 1420, 1311, 1267, 1173, 976, 768, 637;

ESI-MS: [M+H]$^+$: 443.2; [M+Na]$^+$: 465.2;

$^1$H-NMR (DMSO-d6): δ 8.45 (s, 1H, Ar—H), 7.94 (s, 1H, —NH2), 7.88 (dd, 1H, Ar—H), 7.25 (s, 1H, —NH2), 6.98 (d, 1H, Ar—H), 6.55 (s, 8H, 8×HOOC—CH=), 4.37 (s, 2H,

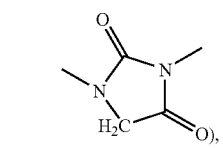), 4.29 (t, 2H,

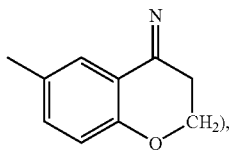

3.41 (t, 3H, Ar—CH3), 3.32 (t, 2H,

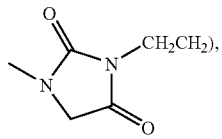

2.88 (t, 2H,

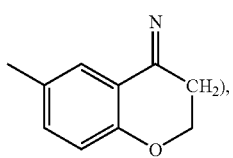

2.47-2.55 (s, 8H,

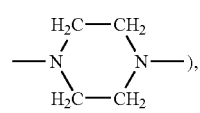), 2.31-2.35 (m, 5H,

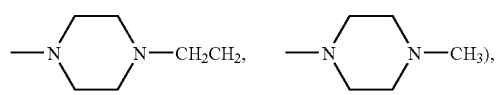

1.37-1.51 (m, 4H,

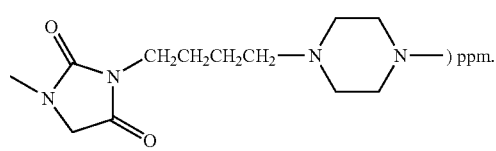) ppm.

Example 5

1-[4-(2,3-dihydro-6-methoxy)benzopyran]imino-3-(4-piperidine) butyl-2,4-imidazole dione

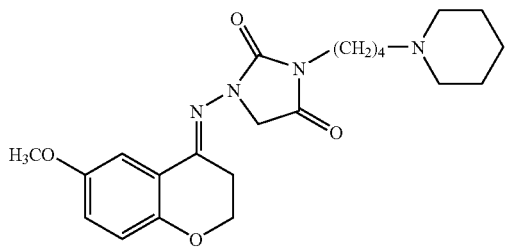

processing as the method in the example 1, except for 1-amino-3-[(4-piperidine) butyl]-2,4-imidazole dione in place of 1-amido-3-[4-(4-methyl-1-piperazine) butyl]-2,4-imidazole dione, to obtain the title compound in the forms of light yellow oil 0.26 g, yield: 22.41%.

IR (KBr, cm$^{-1}$): 2932, 1771, 1712, 1489, 1442, 1205, 1044, 756, 743;

EI-MS: m/z 413: M−H]$^{\pm}$; m/z 237:

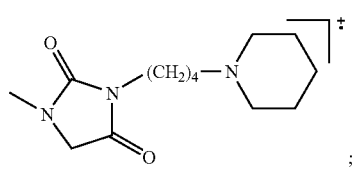

m/z 98 (Base Peak):

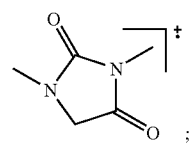

$^1$H-NMR (CDCl$_3$): δ 7.48 (d, 1H, Ar—H), 6.98 (dd, 1H, Ar—H), 6.85 (d, 1H, Ar—H), 4.31 (s, 2H,

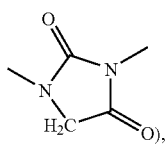

4.26 (t, 2H,

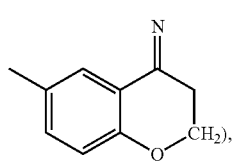

3.80 (s, 3H, —OCH3), 3.57 (t, 2H,

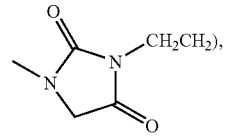

2.96 (t, 2H,

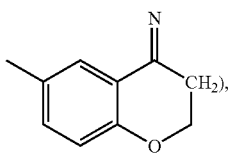

2.44-2.550 (m, 6H,

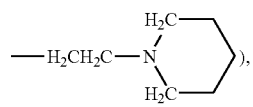

1.63-1.70 (m, 8H,

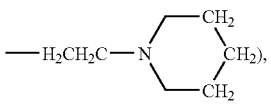

1.26 (t, 2H,

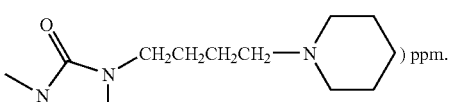 ) ppm.

Example 6

1-[4-(2,3-dihydro-6-chloro) benzopyran]imino-3-(4-piperidine) butyl-2,4-imidazole dione

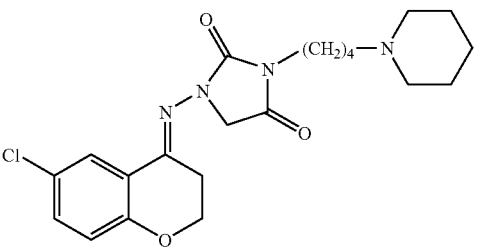

processing as the method in the example 2, except for in the step (3), 1-amino-3-[(4-piperidine) butyl]-2,4-imidazole dione in place of 1-amino-3-[4-(4-methyl-1-piperazine) butyl]-2,4-imidazole dione, to obtain the title compound in the forms of oil 0.20 g, yield: 17.7%.

IR (KBr, cm$^{-1}$): 2936, 1775, 1713, 1443, 1414, 1286, 1038, 918, 820, 734;

EI-MS: m/z 417: M−H]$^{\ddagger}$; m/z 237:

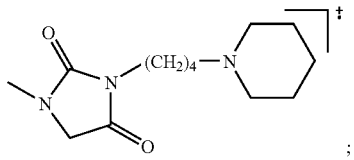

m/z 98 (Base Peak):

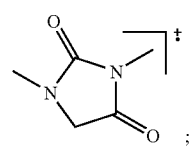

$^{1}$H-NMR (CDCl$_3$): δ 7.95 (s, 1H, Ar—H), 7.27 (dd, 1H, Ar—H), 6.84 (d, 1H, Ar—H), 4.25-4.29 (m, 4H,

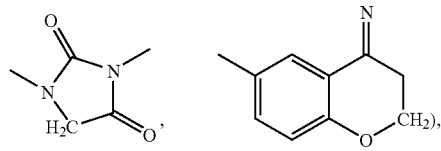

3.53 (t, 2H 2.94 (t, 2H,

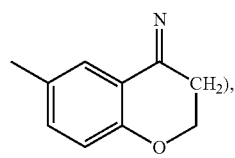

2.66 (d, 6H,

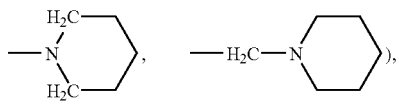

1.71 (m, 4H,

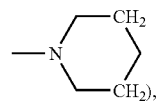

1.65 (m, 4H,

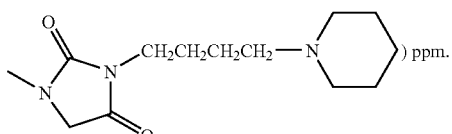

1.49 (s, 2H,

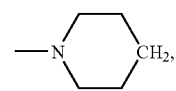) ppm.

Example 7

1-[4-(2,3-dihydro-6-methyl)benzopyran]imino-3-(4-piperidine) butyl-2,4-imidazole dione

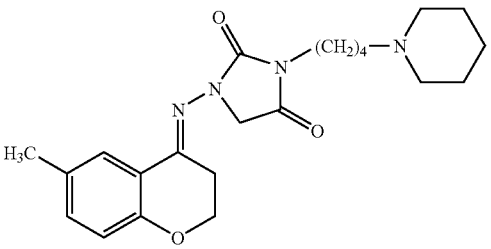

processing as the method in the example 3, except for in the step (3), 1-amino-3-[(4-piperidine) butyl]-2,4-imidazole dione in place of 1-amino-3-[4-(4-methyl-1-piperazine) butyl]-2,4-imidazole dione, to obtain the title compound in the forms of oil 0.20 g, yield: 25.12%.

IR (KBr, cm$^{-1}$): 2934, 1770, 1712, 1492, 1443, 1414, 1298, 1220, 1041, 818, 743;

EI-MS: m/z 397: M—H]⁺; m/z 237:

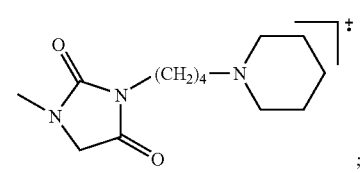

m/z 98 (Base Peak):

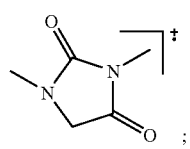

¹H-NMR (CDCl₃): δ 7.79 (s, 1H, Ar—H), 7.16 (dd, 1H, Ar—H), 6.82 (d, 1H, Ar—H), 4.24-4.27 (m, 4H,

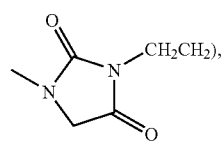

3.55 (t, 2H,

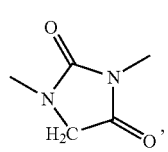

2.94 (t, 2H,

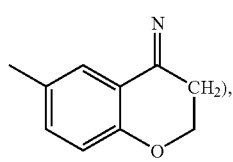

2.53 (s, 4H,

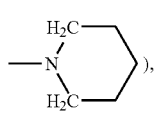

2.47 (t, 2H,

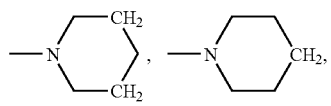

2.27 (s, 3H, —CH3), 1.61-1.68 (m, 8H,

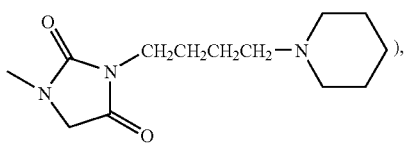

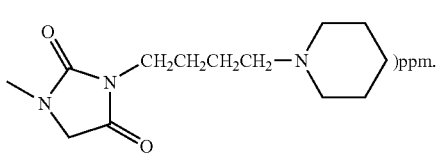

1.46 (s, 2H,

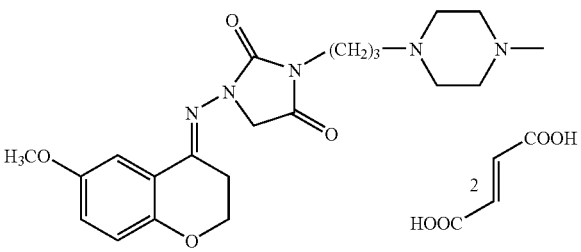

)ppm.

Example 8

1-[4-(2,3-dihydro-6-methoxy)benzopyran]imino-3-[3-(4-methyl piperazine-1-yl)propyl]-2,4-imidazole dione difumarate processing as the method in the example 1, except for in the step (3), 1-amino-3-[3-methyl-1-piperazine]]propyl]-2,4-imidazole dione in place of 1-amino-3-[4-(4-methyl-1-piperazine) butyl]-2,4-imidazole dione, to obtain the title compound in the forms of white powder 0.30 g, m.p.: 220-221° C., yield: 15.46%.

IR (KBr, cm⁻¹): 2438, 1721, 1709, 1491, 1450, 1292, 1171, 1024, 977, 758, 640;

EI-MS: m/z 413: M–H]$^{\pm}$, m/z 238:

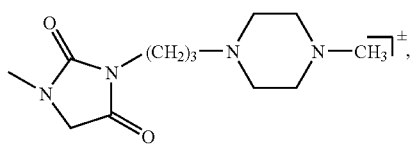

m/z 43 (Base Peak): —(CH2)3-]$^{\pm}$;

$^1$H-NMR (DMSO-d6): δ 7.39 (d, 1H, Ar—H), 7.03 (dd, 1H, Ar—H), 6.90 (d, 1H, Ar—H), 6.59 (s, 4H, 4×HOOC—CH=), 4.35 (s, 2H,

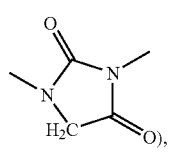

4.20 (t, 2H,

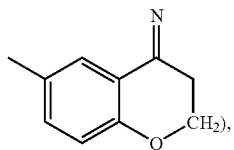

3.72 (s, 3H, —OCH3), 3.45 (t, 2H,

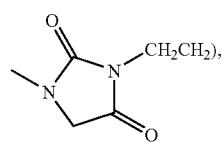

2.86 (t, 2H,

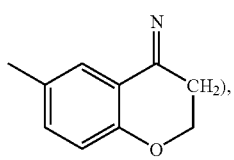

2.35 (s, 3H,

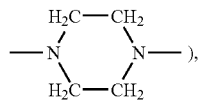

2.34 (t, 2H,

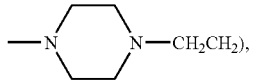

2.28 (s, 3H,

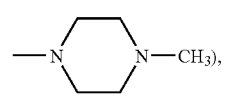

1.70 (five, 2H,

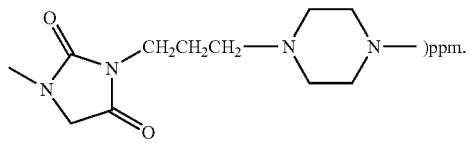

)ppm.

Example 9

1-[4-(2,3-dihydro-6-methyl)benzopyran]imino-3-[3-(4-methyl piperazine-1-)propyl]-2,4-imidazole dione difumarate

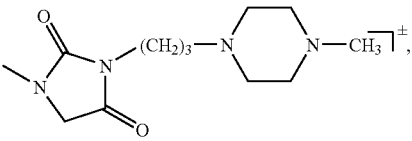

processing as the method in the example 1, except for in the step (3), 1-amino-3-[3-(4-methyl-1-piperazine) propyl]-2,4-imidazole dione in place of 1-amino-3-[4-(4-methyl-1-piperazine) butyl]-2,4-imidazole dione, to obtain the title compound in the forms of white thin needle crystal 0.23 g, m.p.: 237-239° C., yield: 18.40%.

IR (KBr, cm$^{-1}$): 1775, 1709, 1447, 1411, 1301, 1174, 975, 770, 635;

EI-MS: m/z 397: M–H]$^{\pm}$, m/z 238:

m/z 43 (Base Peak): —(CH2)3-]$^{\pm}$;

$^1$H-NMR (DMSO-d6): δ 12.5-13.5 (w, 4H, 4-COOH), 7.72 (d, 1H, Ar—H), 7.22 (dd, 1H, Ar—H), 6.85 (d, 1H, Ar—H), 6.59 (s, 4H, 4×HOOC—CH=), 4.34 (s, 2H,

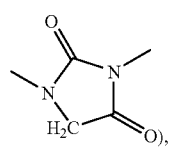

4.22 (t, 2H, 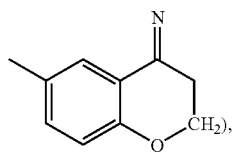

3.45 (t, 2H, 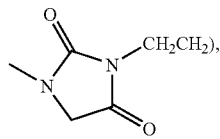

2.87 (t, 2H, 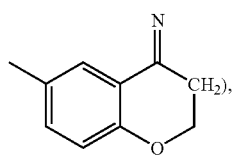

2.34-2.46 (m, 6H, 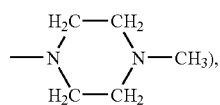

2.33 (t, 2H, 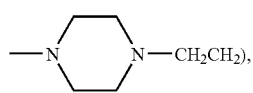

2.08 (s, 6H, 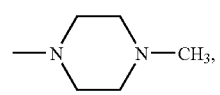

Ar—CH3), 1.70 (m, 2H,

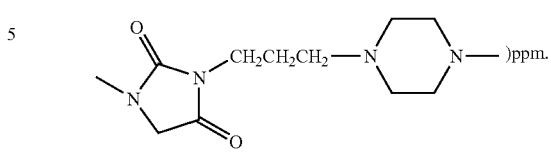)ppm.

Example 10

1-[4-(2,3-dihydro-6-chlorine) benzopyran]imino-3-[3-(4-methyl piperazine-1-yl)propyl]-2,4-imidazole dione difumarate processing as the method in the example 1, except for in the step (3), 1-amino-3-[3-(4-methyl-1-piperazine) propyl]-2,4-imidazole dione in place of 1-amino-3-[4-(4-methyl-1-piperazine) butyl]-2,4-imidazole dione, to obtain the title compound in the forms of white thin needle crystal 0.32 g, m.p.: 232-234° C., yield: 28.32%.

IR (KBr, cm$^{-1}$): 1709, 1412, 1302, 1289, 1175, 975, 786, 769, 636;

EI-MS: m/z 417: M−H↑$^{\pm}$; m/z 238 (Base Peak):

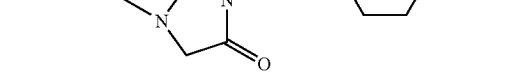

m/z:

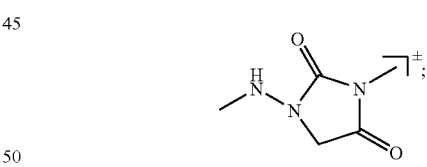

m/z: m/z 43: —(CH$_2$)$_3$-↑$^{\pm}$;

$^1$H-NMR (DMSO-d6), δ: 12.5-13.5 (w, 4H, 4-COOH), 7.87 (d, 1H, Ar—H), 7.44 (dd, 1H, Ar—H), 7.02 (d, 1H, Ar—H), 6.60 (s, 4H, 4×HOOC—CH═), 4.37 (s, 2H,

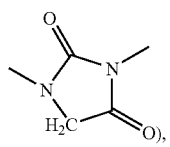

4.28 (t, 2H,

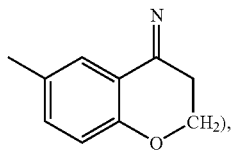

3.47 (t, 2H,

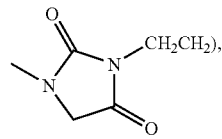

2.89 (t, 2H,

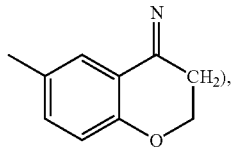

2.23-2.43 (m, 13H,

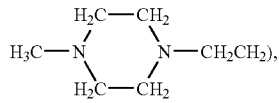

1.70 (m, 2H,

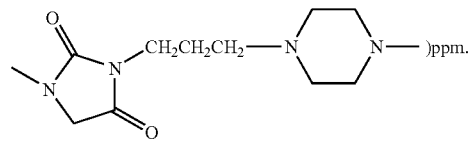)ppm.

Example 11

1-[4-(2,3-dihydro-7-chloro) benzopyran]imino-3-[4-(methyl-1-piperazine) butyl]-2,4-imidazole dione difumarate

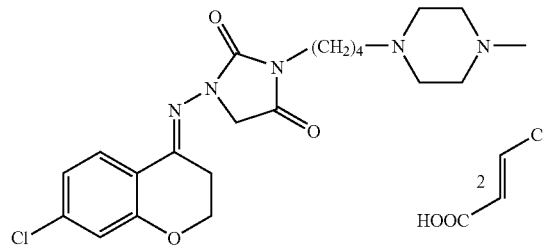

processing as the method in the example 1, except for in the step (1), m-chloro phenol in place of para-hydroxybenzene methyl ether, to obtain the title compound in the forms of white powder 0.53 g, yield: 46.08%.

IR (KBr, cm$^{-1}$): 3420, 2389, 2955, 1712, 1417, 1309, 979, 763, 639;

ESI-MS: [M+H]+: 434.2 (isotope peak: 436.1);

1H-NMR (DMSO-d6), δ: 10.5-14.5 (w, 4H, 4-COOH), 7.86 (s, 1H, Ar—H), 7.45 (dd, 1H, Ar—H), 7.43 (d, 1H, Ar—H), 6.58 (s, 4H, 4×HOOC—CH═), 4.39 (s, 2H,

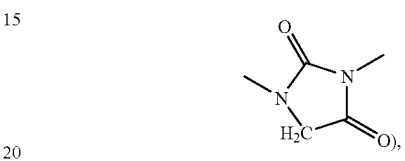), 4.28 (t, 2H,

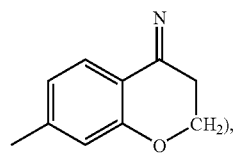

3.43 (t, 2H,

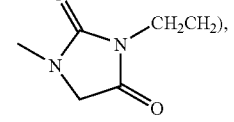

2.90 (t, 2H,

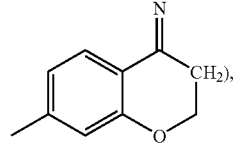

2.50-2.58 (m, 5H,

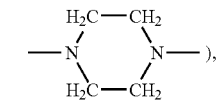

2.49 (s, 3H,

—N(CH₂CH₂)₂N— ), 2.38 (t, 2H,

—N(piperazine)—CH₂CH₂), 2.32 (s, 3H,

—N(piperazine)—CH₃), 1.55 (m, 2H, methyl-imidazolidinedione-N-CH₂CH₂CH₂CH₂-piperazine-N— ), 1.44 (m, 2H, methyl-imidazolidinedione-N-CH₂CH₂CH₂CH₂-piperazine-N— )ppm.

Example 12

1-[4-(2,3-dihydro-7-methyl)benzopyran]imino-3-(2-imidazole) ethyl-2,4-imidazole dione difumarate

[structure: 1-methyl-3-(4-(4-methylpiperazin-1-yl)butyl)-imidazolidine-2,4-dione with N=7-methylchroman-4-ylidene]

[fumaric acid · 2, HOOC–CH=CH–COOH]

processing as the method in the example 1, except for in the step (1), m-methyl phenol in place of para-hydroxybenzene methyl ether, to obtain the title compound in the forms of yellow oil 0.27 g, yield: 25.82%.

IR (KBr, cm⁻¹): 2934, 1770, 1712, 1492, 1443, 1414, 1298, 1220, 1041, 818, 743;

EI-MS: m/z 352: M–H]⁺; m/z 98 (Base Peak):

[structure: 1,3-dimethyl-imidazolidine-2,4-dione cation];

1H-NMR (CDCl₃), δ: 7.79 (s, 1H, Ar—H), 7.54 (m, 1H,

[imidazole-2-H]), 7.16 (dd, 1H, Ar—H), 7.01 (m, 2H,

[imidazole-4,5-H]), 6.82 (d, 1H, Ar—H), 4.24-4.27 (m, 4H,

[methyl-imidazolidinedione + 7-methylchroman-O-CH₂]), 3.55 (t, 2H,

[methyl-imidazolidinedione-N-CH₂CH₂]), 2.94 (t, 2H,

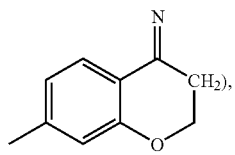

2.47 (t, 2H,

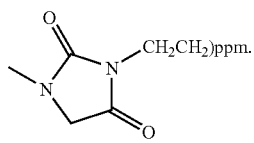

Example 13

1-[4-(2,3-dihydro-6-carbamoyl)sulfo-benzopyran]imino-3-[4-(methyl-1-piperazine) butyl]-2,4-imidazole dione difumarate

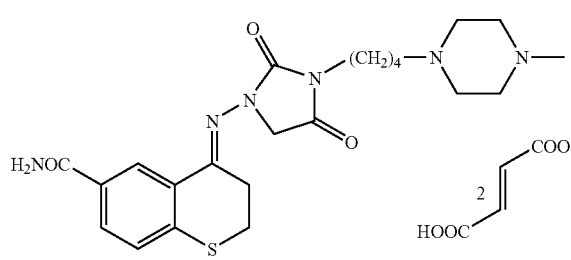

processing as the method in the example 6, using para-hydrosulphonyl benzamide as starting material, to obtain 6-carbamoyl-2,3-dihydro-4H-1-sulfo-benzopyran-4-one in the forms of yellow crystal 1.97 g, yield: 75.73%.

IR (KBr, cm$^{-1}$): 3421, 1678, 1646, 1612, 1371, 1289, 1141, 1021, 926, 782, 611.

ESI-MS: [M+H]+: 192.1, [M+Na]+: 214.0.

To obtain the title compound of yellow powder 0.28 g, yield: 26.26%.

IR (KBr, cm$^{-1}$): 3473, 2949, 2422, 1705, 1420, 1311, 1267, 1173, 976, 768, 637.

ESI-MS: [M+H]+: 443.2; [M+Na]+: 465.2.

$^{1}$H-NMR (DMSO-d6), δ: 8.45 (s, 1H, Ar—H), 7.94 (s, 1H, —NH2), 7.88 (dd, 1H, Ar—H), 7.25 (s, 1H, —NH2), 6.98 (d, 1H, Ar—H), 6.55 (s, 8H, 8×HOOC—CH═), 4.37 (s, 2H,

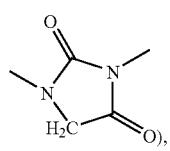

4.39 (t, 2H,

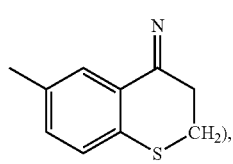

3.41 (t, 3H, Ar—CH3), 3.32 (t, 2H,

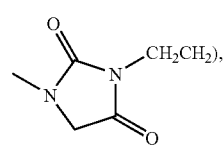

2.98 (t, 2H,

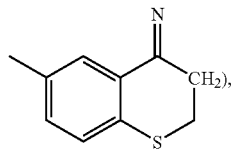

2.47-2.55 (s, 8H,

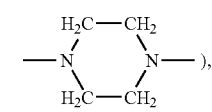

2.31-2.35 (m, 5H,

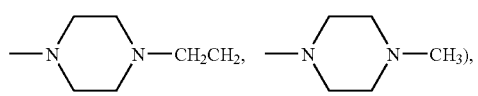

1.37-1.51 (m, 4H,

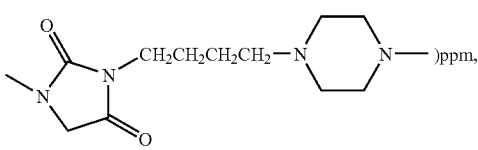

EXAMPLES FOR THE COMPOUNDS OF FORMULA (Ib)

Example 14

1-[4-(2,3-dihydro-6-hydroxy)benzopyran]imino-3-[4-(methyl-1-piperazine) butyl]-2,4-imidazole dione difumarate

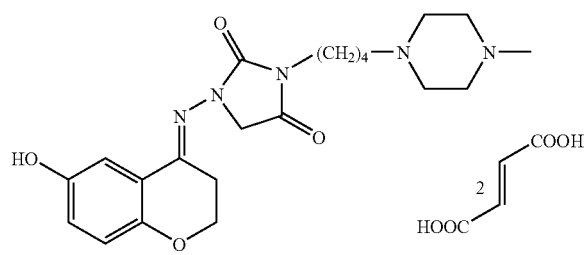

(1) Preparation of 3-(4-methoxyphenoxy)propanoic acid

Solid KOH 6.80 g, (0.122 mol) and H$_2$O (10 ml) are added to para-methoxyphenol 7.0 g (0.0564 mol), the resultant mixture is stirred at the room temperature while 3-chloropropanoic acid (6.12 g, 0.0564 mol) is added to thereof. Then the mixture is stirred and heated to reflux for 3 h. The reaction solution is acidified to pH 2 by adding concentrated aqueous HCl and extracted with ether. The combined ether extracts is then washed with 10% aqueous NaHCO$_3$ and acidified to pH 3-4 by adding concentrated aqueous HCl, and precipitate is formed. The residue is filtered and recrystallized by benzene to provide needle crystal 2.0 g. m.p.: 102-103° C., yield: 18.1%.

(2) Preparation of 2,3-dihydro-6-methoxy-benzopyran-4-one

Polyphosphonic acid (45 ml) is added to 3-(4-methoxyphenoxy)propanoic acid 2.0 g (0.010 mol). The mixture is stirred and heated for 2 h. To the mixture, 15 g debris ice is added. The reaction mixture was extracted with ethyl acetate and the combined ethyl acetate extracts are washed with 10% aqueous NaHCO$_3$ to almost neutral, dried over Na$_2$SO$_4$, concentrated and cooled to provide crystal, which is recrystallized from ethyl acetate to provide white needle crystal 1.63 g. m.p.: 44-45° C., yield 91.6%.

(3) Preparation of 2,3-dihydro-6-hydroxy benzopyran-4-one

Glacial acetic acid and HBr (>40%) each 20 ml are successively added to methoxy benzopyran-4-one 2.9 g (0.0163 mol), stirred and refluxed for 1 h, and then the reactant liquor is modulated pH for 10-11 by KOH, the water layer is modulated pH for 2-3 by concentrated hydrochloric acid, and then extracted by ethyl acetate; the organic layers are combined and dried over anhydrous Na$_2$SO$_4$, cooled to precipitate black solid, and recrystallized by ethyl acetate, to obtain bright yellow crystal 2.17 g, m.p.: 142-144° C., yield: 81.2%.

(4) Preparation of Title Compound

Anhydrous methanol 10 mL and glacial acetic acid are added to 1-amino-3-[4-(4-methyl-1-piperazine) butyl]-2,4-imidazole dione 0.85 g (0.0316 mol), and then the solution of 2,3-dihydro-6-hydroxybenzopyran-4-one 0.52 (0.00316 mol) in 10 mL methanol is dropped. The mixture is heated to reflux for 12.5 hr, and then modulated the pH for 7 by aqueous NaOH, extracted by chloroform. The organic layer is dried over Na$_2$SO$_4$, concentrated and treated with fumaric acid to form light yellow precipitate. The residue is filtered and recrystallized by anhydrous ethanol to provide white like powder 0.51 g, m.p.: 203-205° C., yield: 45.54%.

IR (KBr, cm$^{-1}$): 3407, 2390, 1707, 1453, 1305, 1265, 1176, 979, 763, 637.

ESI-MS: [M+H]+: 416.2, [M+Na]+: 438.1.

$^1$H-NMR (DMSO-d6), δ: 7.32 (d, 1H, Ar—H), 6.78-7.07 (m, 2H, Ar—H), 6.58 (s, 4H, 4×HOOC—CH=), 4.34 (s, 2H,

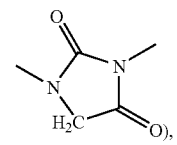

4.17 (t, 2H,

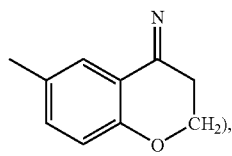

3.42 (t, 2H,

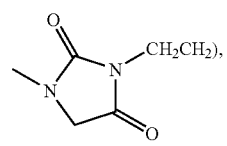

2.84 (t, 2H,

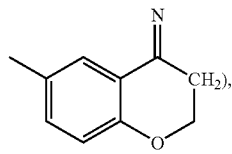

2.50-2.54 (m, 8H,

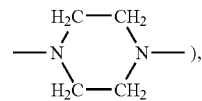

2.33-2.35 (m, 5H,

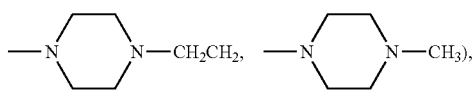

1.55 (m, 2H,

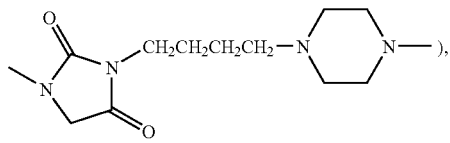

1.45 (m, 2H,

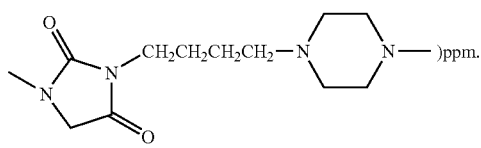

Example 15

1-[4-(2,3-dihydro-6-ethoxy)benzopyran]imino-3-[4-(methyl-1-piperazine) butyl]-2,4-imidazole dione difumarate

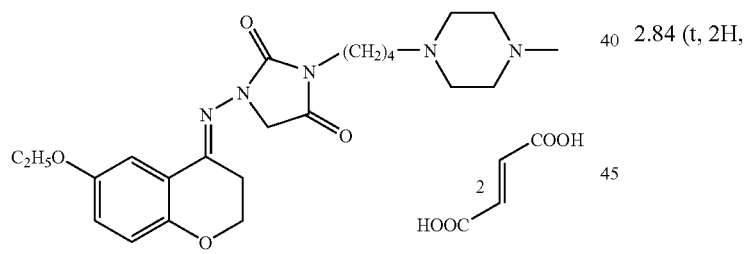

preparation of 2,3-dihydro-6-ethoxy benzopyran-4-one ethyl bromide 1.66 g, K$_2$CO$_3$ 1.26 g (0.0092 mol) and acetone 50 mL are added to the 2,3-dihydro-6-hydroxybenzopyran-4-one 1.0 g (0.0061 mol), stirred and refluxed for 4 h, and then cooled to room temperature, the white like solid is filtered, and the solid is washed by 10% aqueous KOH and water. The organic layer is dried over anhydrous Na$_2$SO$_4$, concentrated and cooled to precipitate white like needle crystal. The residue are filtered and recrystallized by petroleum ether, to obtain light yellow needle crystal 0.77 g, m.p.: 60-62° C., yield: 70.94%.

Preparation of Title Compound: Processing as the Method of example 14, 2,3-dihydro-6-ethoxy benzopyran-4-one is reacted with 1-amino-3-[4-(4-methyl-1-piperazine) butyl]-2,4-imidazole dione, to obtain white powder of the title compound 0.39 g, m.p.: 225-227° C., yield: 36.11%.

IR (KBr, cm$^{-1}$): 3409, 2977, 2413, 1715, 1451, 1299, 763, 638.

ESI-MS: [M+H]+: 444.2.

$^1$H-NMR (DMSO-d6), δ: 7.35 (d, 1H, Ar—H), 6.99 (dd, 1H, Ar—H), 6.87 (d, 1H, Ar—H), 6.55 (s, 4H, 4×HOOC—CH=), 4.33 (s, 2H,

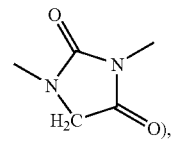

4.17 (t, 2H,

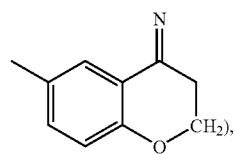

3.94 (q, 2H, —OCH2CH3), 3.40 (t, 2H,

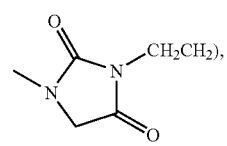

2.84 (t, 2H,

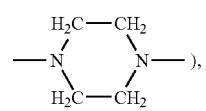

2.54 (s, 5H,

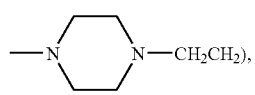

2.47 (t, 2H, 2.33 (s, 3H, 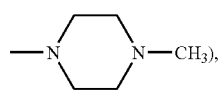

1.53 (m, 2H, 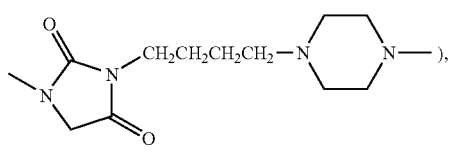

1.41 (m, 2H, 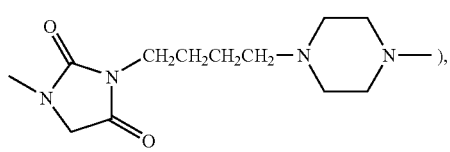

1.27 (t, 3H, —OCH2CH3) ppm.

Example 16

1-[4-(2,3-dihydro-6-propoxy-)benzopyran]imino-3-[4-(methyl-1-piperazine) butyl]-2,4-imidazole dione difumarate

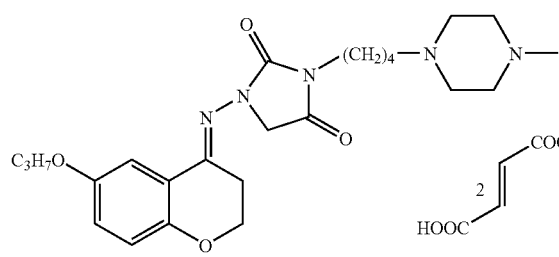

processing as the method of example 14, except for in the step (1), bromine propane in place of ethyl bromide, to obtain light yellow solid of 2,3-dihydro-6-propoxy-benzopyran-4-one 0.67 g, m.p.: 50-52° C., yield: 67.96%.

preparation of compound: processing as the step (4) in the example 14, 2,3-dihydro-6-propoxy-benzopyran-4-ketone is reacted with 1-amino-3-[4-(4-methyl-1-piperazine) butyl]-2,4-imidazole dione, to obtain light yellow powder of the title compound 0.85 g, m.p.: 218-20° C., yield: 61.68%.

IR (KBr, cm$^{-1}$): 3484, 2965, 2425, 1714, 1448, 1299, 982, 763, 638.

ESI-MS: [M+H]+: 458.2.

$^{1}$H-NMR (DMSO-d6), δ: 7.35 (d, 1H, Ar—H), 7.00 (dd, 1H, Ar—H), 6.87 (d, 1H, Ar—H), 6.55 (s, 4H, 4×HOOC—CH=), 4.34 (s, 2H, 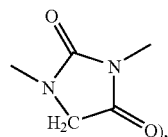

4.17 (t, 2H, 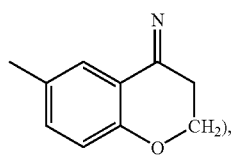

3.83 (q, 2H, —OCH2CH3), 3.40 (t, 2H, 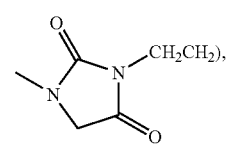

2.84 (t, 2H, 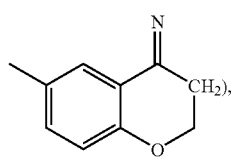

2.65 (s, 4H, 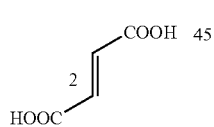

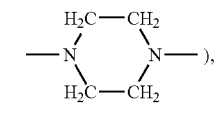

2.48 (s, 4H, 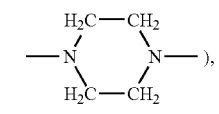

2.37 (m, 5H, 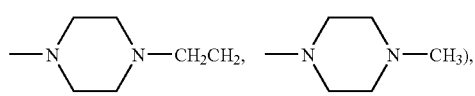

1.70 (m, 2H, —OCH2CH2CH3), 1.53 (m, 2H,

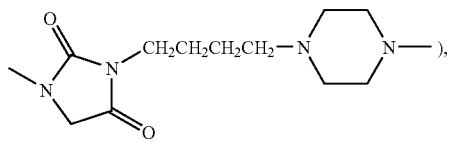

1.42 (m, 2H,

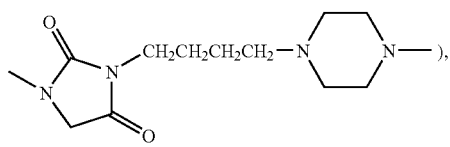

0.93 (t, 3H, —OCH2CH2CH3) ppm.

Example 17

1-[4-(2,3-dihydro-6-butoxy)benzopyran]imino-3-[4-(methyl-1-piperazine) butyl]-2,4-imidazole dione difumarate

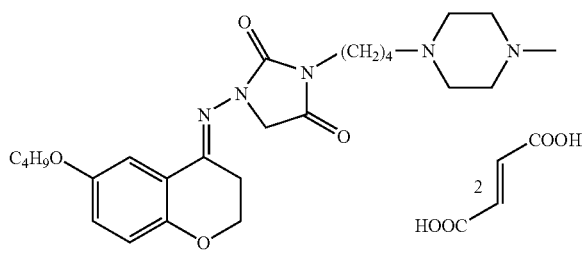

(1) processing as the method of example 15, except for in the step (1), bromine butane in place of ethyl bromide, to obtain light yellow solid of 2,3-dihydro-6-propoxy-benzopyran-4-one 0.67 g, m.p.: 50-52° C., yield: 67.96%.

(2) preparation of compound: processing as the step (4) in the example 14, 2,3-dihydro-6-propoxy-benzopyran-4-one is reacted with 1-amino-3-[4-(4-methyl-1-piperazine) butyl]-2,4-imidazole dione, to obtain white like powder of the title compound 0.41 g, m.p.: 208-210° C., yield: 60.35%.

IR (KBr, cm$^{-1}$): 3448, 2953, 1714, 1446, 1298, 1179, 637.
ESI-MS: [M+H]+: 472.3.
$^1$H-NMR (DMSO-d6), δ: 11-13 (w, 4H, —COOH), 7.38 (d, 1H, Ar—H), 7.02 (dd, 1H, Ar—H), 6.88 (d, 1H, Ar—H), 6.58 (s, 4H, 4×HOOC—CH=), 4.36 (s, 2H,

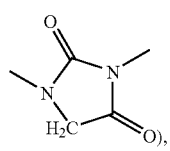

4.18 (t, 2H,

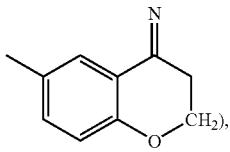

3.89 (q, 2H, —OCH2CH3), 3.41 (t, 2H,

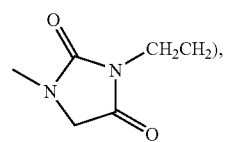

2.87 (t, 2H,

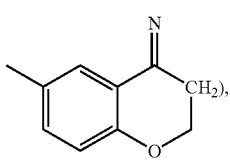

2.50 (s, 6H,

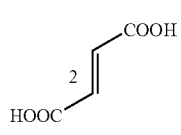

2.32 (t, 2H,

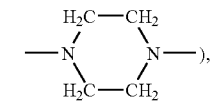

2.26 (s, 3H,

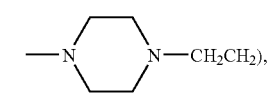

1.67 (m, 2H, —OCH2CH2CH2CH3), 1.43 (m, 2H,

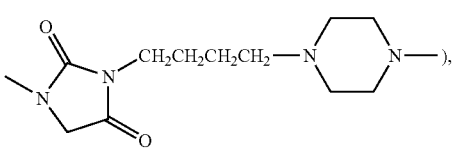

1.41 (m, 4H,

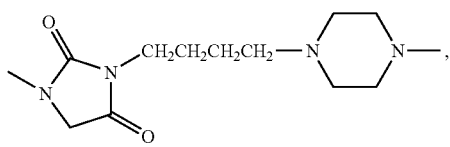

OCH2CH2CH2CH3), 0.92 (t, 3H, —OCH2CH2CH2CH3) ppm.

Example 18

1-[4-(2,3-dihydro-6-ethoxy)benzopyran]imino-3-(4-piperidine) butyl-2,4-imidazole dione

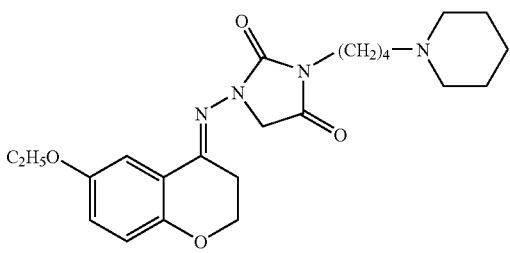

processing as the method in the example 14, except for in step (4) 1-amino-3-[(4-piperidine) butyl]-2,4-imidazole dione in place of 1-amino-3-[4-(4-methyl-1-piperazine) butyl]-2,4-imidazole dione, to obtain light yellow oil of the title compound 0.27 g, yield: 41.34%.

IR (KBr, cm$^{-1}$): 2936, 1772, 1712, 1491, 1442, 1415, 1205, 1046, 961, 766, 747.

EI-MS: m/z 427: M−H]$^{+}$; m/z 237:

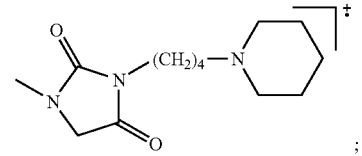

m/z 98 (Base Peak):

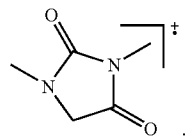

$^1$H-NMR (CDCl$_3$), δ: 7.46 (d, 1H, Ar—H), 6.96 (dd, 1H, Ar—H), 6.83 (d, 1H, Ar—H), 4.30 (s, 2H,

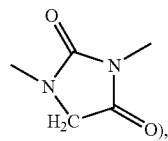

4.24 (t, 2H,

4.00 (q, 2H, —OCH2CH3), 3.55 (t, 2H,

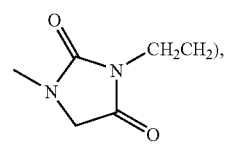

2.94 (t, 2H,

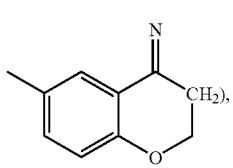

2.79 (s, 4H,

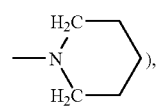

2.72 (t, 2H,

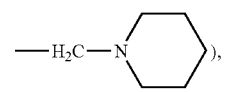

1.76 (m, 4H,

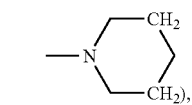

1.69 (s, 4H, 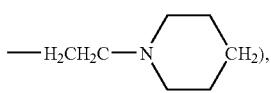

1.53 (t, 2H, 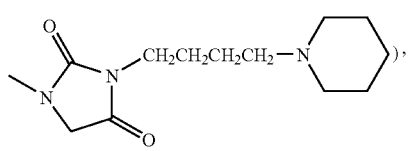

1.38 (t, 3H, —OCH2CH3) ppm.

Example 19

1-[4-(2,3-dihydro-6-propoxy-)benzopyran]imino-3-(4-piperidine) butyl-2,4-imidazole dione

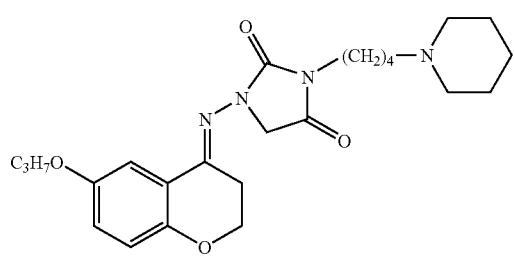

processing as the method in the example 14, except for in step (4), 1-amino-3-[(4-piperidine)butyl]-2,4-imidazole dione in place of 1-amino-3-[4-(4-methyl-1-piperazine) butyl]-2,4-imidazole dione, to obtain light yellow oil of the title compound 0.34 g, yield: 52.71%.

IR (KBr, cm$^{-1}$): 2938, 1773, 1712, 1573, 1491, 1437, 1411, 1202, 1043.

EI-MS: m/z 441: M−H]$^+$; m/z 237:

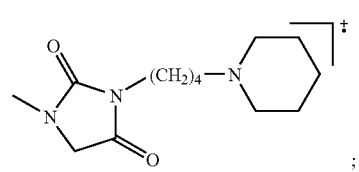

m/z 98 (Base Peak):

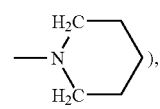

$^1$H-NMR (CDCl$_3$), δ: 7.54 (s, 1H, Ar—H), 6.96 (dd, 1H, Ar—H), 6.82 (d, 1H, Ar—H), 4.29 (s, 2H,

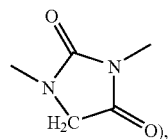

4.23 (t, 2H,

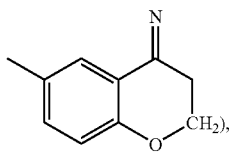

3.88 (t, 2H, —OCH2CH2CH3), 3.55 (t, 2H,

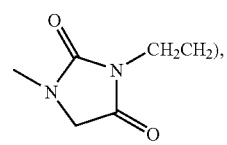

2.94 (t, 2H,

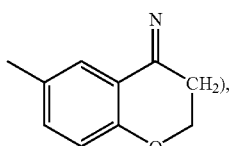

2.81 (s, 4H,

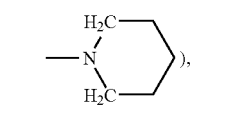

2.74 (t, 2H,

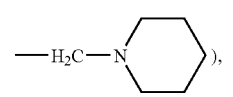

1.76 (m, 4H,

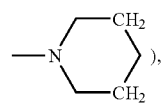

1.69 (s, 4H, 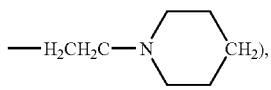

1.53 (t, 2H, 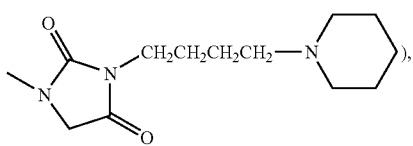

1.22 (t, 2H, —OCH2CH2CH3), 0.99 (t, 3H, —OCH2CH3) ppm.

Example 20

1-[4-(2,3-dihydro-6-butoxy)benzopyran]imino-3-(4-piperidine) butyl-2,4-imidazole dione

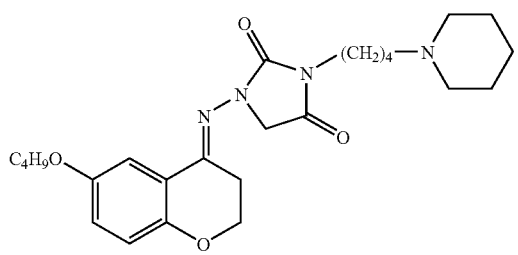

processing as the method in the example 14, except for in step (4), 1-amino-3-[(4-piperidine) butyl]-2,4-imidazole dione in place of 1-amino-3-[4-(4-methyl-1-piperazine) butyl]-2,4-imidazole dione, to obtain light yellow oil of the title compound 0.51 g, yield: 56.04%.

IR (KBr, cm$^{-1}$): 2934, 1774, 1712, 1596, 1489, 1441, 1413, 1204, 1042, 822, 768.

EI-MS: m/z 455: M–H]$^{\pm}$; m/z 237:

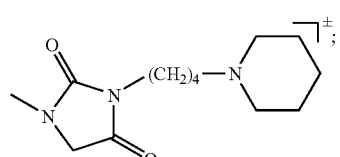

m/z 98 (Base Peak):

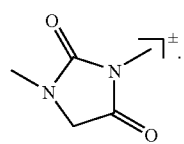

$^1$H-NMR (CDCl$_3$), δ: 7.44 (s, 1H, Ar—H), 6.94 (dd, 1H, Ar—H), 6.82 (d, 1H, Ar—H), 4.28 (s, 2H, 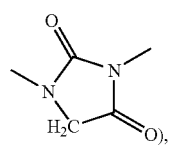

4.23 (t, 2H, 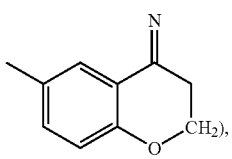

3.92 (t, 2H, —OCH2CH2CH2CH3), 3.55 (t, 2H, 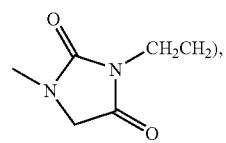

2.92 (t, 2H, 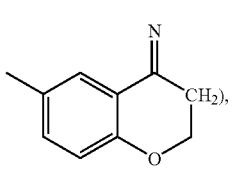

2.81 (s, 4H, 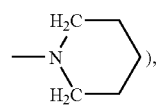

2.74 (t, 2H, 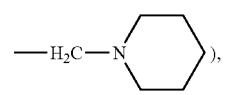

1.46-1.72 (m, 10H, 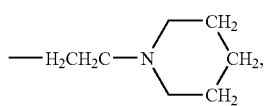

-continued

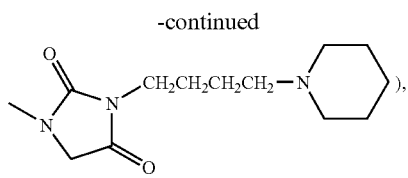

1.19-1.22 (m, 4H, —OCH2CH2CH2CH3), 0.93 (t, 3H, —OCH2CH2CH3) ppm.

Example 21

1-[4-(2,3-dihydro-6-hydroxy)benzopyran]imino-3-(4-piperidine) butyl-2,4-imidazole dione

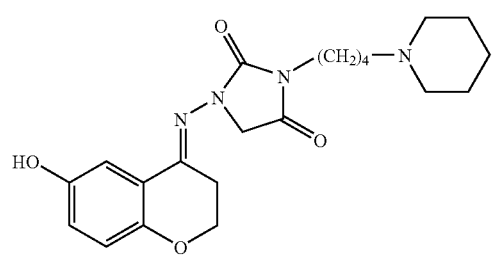

processing as the method in the example 14, except for in step (4), 1-amino-3-[(4-piperidine)butyl]-2,4-imidazole dione in place of 1-amino-3-[4-(4-methyl-1-piperazine) butyl]-2,4-imidazole dione, to obtain light yellow oil of the title compound 0.46 g, yield: 38.3%.

IR (KBr, cm$^{-1}$): 3556, 2937, 1774, 1713, 1594, 1446, 1413, 1040, 911, 823, 731.

EI-MS: m/z 400: M↑$^\pm$; m/z 237:

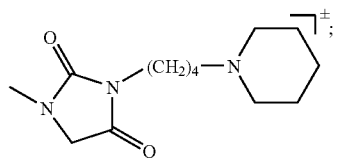

m/z 98 (Base Peak):

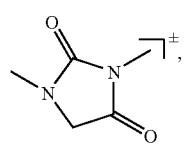

$^1$H-NMR (CDCl$_3$), δ: 7.40 (s, 1H, Ar—H), 6.92 (dd, 1H, Ar—H), 6.77 (d, 1H, Ar—H), 4.5-6.0 (w, 1H, —OH), 4.26 (s, 2H, 2.90 (t, 2H,

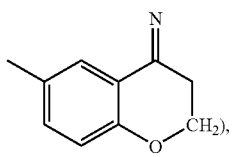

3.53 (t, 2H,

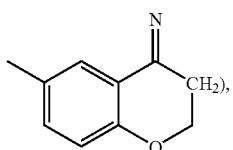

2.90 (t, 2H,

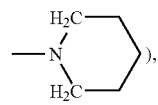

2.89 (s, 4H,

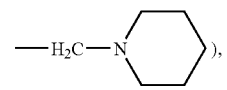

2.71 (t, 2H,

—H$_2$C—N⟨piperidine⟩), 1.66-1.83 (m, 6H,

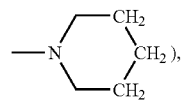

1.64 (m, 2H, 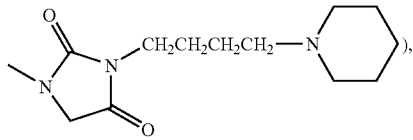

1.60 (s, 2H, 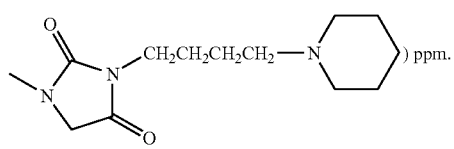) ppm.

Example 22

1-[4-(2,3-dihydro-6-ethoxy)benzopyran]imino-3-[3-(4-methyl piperazine-1-yl)propyl]-2,4-imidazole dione difumarate

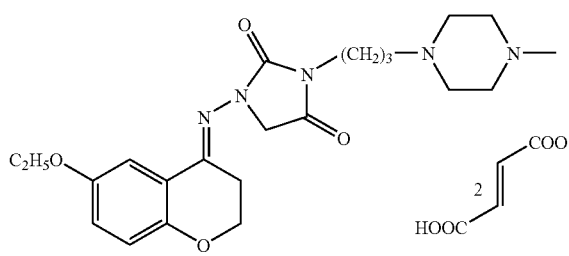

processing as the method in the example 14, except for in step (4), 1-amino-3-[3-(4-methyl-1-piperazine) propyl]-2,4-imidazole dione in place of 1-amino-3-[4-(4-methyl-1-piperazine) butyl]-2,4-imidazole dione, to obtain white loose powder of the title compound 0.35 g, yield: 19.55%.

IR (KBr, cm$^{-1}$): 2984, 1775, 1720, 1710, 1493, 1452, 1292, 1178, 977, 763, 640.

EI-MS: m/z 428: M−H↑$^\pm$, m/z 238:

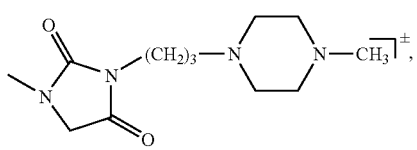

m/z 43 (Base Peak): —(CH$_2$)$_3$↑$^\pm$.

1H-NMR (DMSO-d6), δ: 7.39 (d, 1H, Ar—H), 7.02 (dd, 1H, Ar—H), 6.88 (d, 1H, Ar—H), 6.59 (s, 4H, 4×HOOC—CH═), 4.35 (s, 2H,

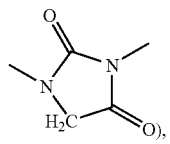

4.20 (t, 2H, 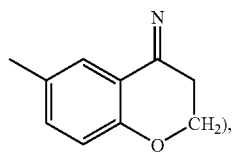

3.95 (q, 3H, —OCH2CH3), 3.47 (t, 2H,

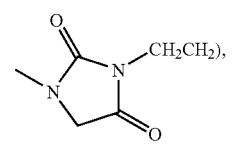

2.87 (t, 2H,

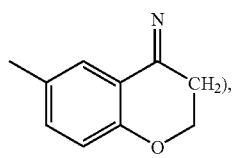

2.53 (s, 4H,

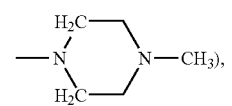

2.49 (s, 4H,

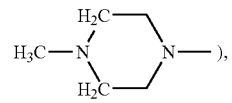

2.35 (t, 2H,

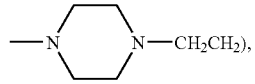

2.29 (s, 3H, 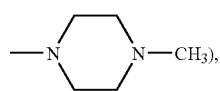), 1.72 (m, 2H, 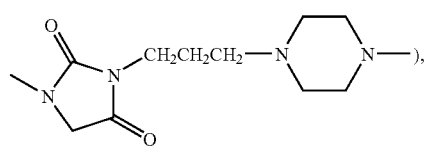), 1.30 (t, 3H, —OCH2CH3) ppm.

Example 23

1-[4-(2,3-dihydro-6-propoxy-)benzopyran]imino-3-[3-(4-methyl piperazine-1-yl)propyl]-2,4-imidazole dione difumarate

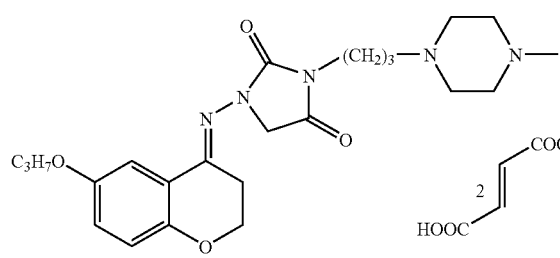

processing as the method in the example 14, except for in step (4), 1-amino-3-[3-(4-methyl-1-piperazine) propyl]-2,4-imidazole dione in place of 1-amino-3-[4-(4-methyl-1-piperazine) butyl]-2,4-imidazole dione, to obtain white loose powder of the title compound 0.43 g, yield: 26.54%.

IR (KBr, cm$^{-1}$): 2963, 2389, 1776, 1722, 1711, 1449, 1288, 1178, 976, 788, 758, 638.

EI-MS: m/z 442: M–H]$^±$, m/z 238:

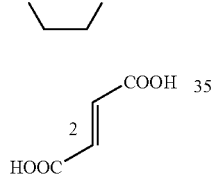

m/z 43 (Base Peak): —(CH$_2$)$_3$]$^±$.

$^1$H-NMR (DMSO-d6), δ: 12.5-13.5 (w, 4H, 4-COOH), 7.39 (d, 1H, Ar—H), 7.02 (dd, 1H, Ar—H), 6.88 (d, 1H, Ar—H), 6.59 (s, 4H, 4×HOOC—CH=), 4.35 (s, 2H,

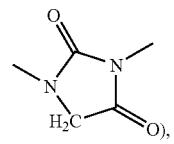), 4.20 (t, 2H,

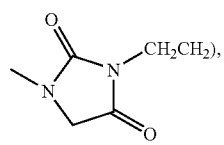), 3.86 (t, 2H, —OCH2CH2CH3), 3.46 (t, 2H,

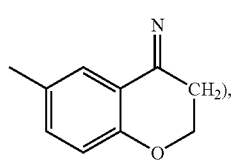), 2.87 (t, 2H,

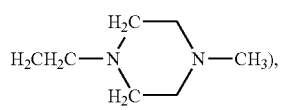), 2.34-2.43 (m, 6H,

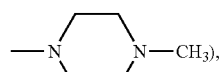), 2.26 (s, 3H,

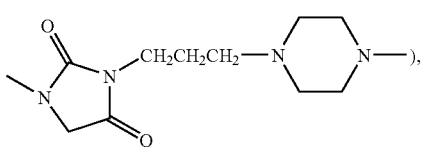), 1.70 (m, 2H, 1.26 (m, 2H, —OCH2CH2CH3), 0.96 (t, 3H, —OCH2CH2CH3) ppm.

Example 24

1-[4-(2,3-dihydro-6-butoxy)benzopyran]imino-3-[3-(4-methyl piperazine-1-yl)propyl]-2,4-imidazole dione difumarate

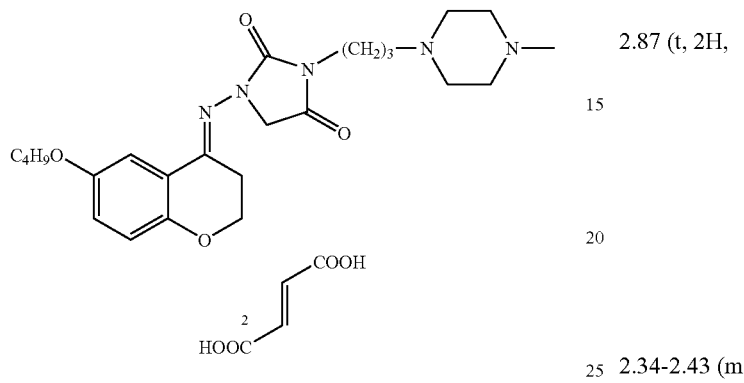

processing as the method in the example 14, except for in step (4), 6-amino-3-[3-(4-methyl-1-piperazine) propyl]-2,4-imidazole dione in place of 1-amino-3-[4-(4-methyl-1-piperazine) butyl]-2,4-imidazole dione, to obtain white loose powder of the title compound 0.35 g, yield: 25.40%.

IR (KBr, cm$^{-1}$): 2959, 2389, 1776, 1722, 1711, 1450, 1292, 1179, 977, 788, 765, 640.

EI-MS: m/z 456: M−H↑$^{\pm}$, m/z 238 (Base Peak):

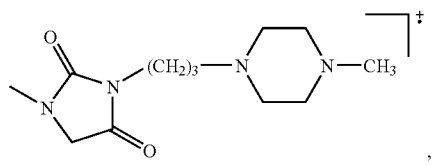

m/z 43: —(CH2)3-↑$^{\pm}$.

$^1$H-NMR (DMSO-d6), δ: 12.5-13.5 (w, 4H, 4-COOH), 7.39 (d, 1H, Ar—H), 7.02 (dd, 1H, Ar—H), 6.88 (d, 1H, Ar—H), 6.60 (s, 4H, 4×HOOC—CH=), 4.35 (s, 2H,

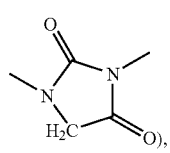

4.20 (t, 2H,

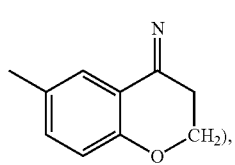

3.90 (t, 2H, —OCH2CH2CH3), 3.46 (t, 2H,

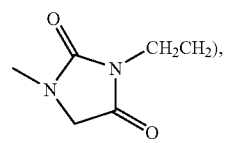

2.87 (t, 2H,

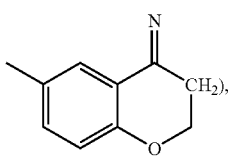

2.34-2.43 (m, 8H,

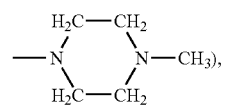

2.33 (t, 2H,

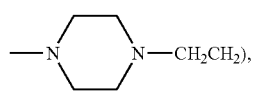

2.25 (s, 3H,

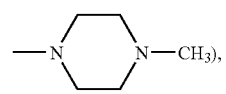

1.67 (m, 4H,

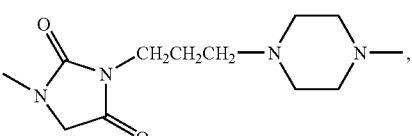

—OCH2CH2CH2CH3), 1.42 (m, 2H, —OCH2CH2CH2CH3), 0.92 (t, 3H, —OCH2CH2CH2CH3) ppm.

Example 25

1-[4-(2,3-dihydro-7-benzyloxy-)benzopyran]imino-3-(4-pyrrole) butyl-2,4-imidazole dione

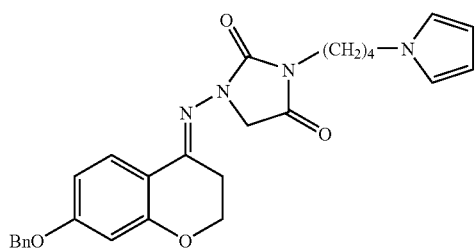

processing as the method in the example 14, except for in step (4), 1-amino-3-[4-(1-pyrrole) butyl]-2,4-imidazole dione in place of 1-amino-3-[4-(4-methyl-1-piperazine) butyl]-2,4-imidazole dione, to obtain yellow solid of (2,3-dihydro-7-benzyloxy-)benzopyran 0.76 g, yield: 56.88%.

to obtain light yellow oil of the title compound 0.51 g, yield: 56.04%

IR (KBr, cm$^{-1}$): 2934, 1774, 1712, 1596, 1489, 1441, 1413, 1204, 1042, 822, 768.

EI-MS: m/z 471: M−H↑$^+$; m/z 98 (Base Peak):

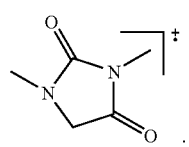

$^1$H-NMR (CDCl$_3$), δ: 7.44 (s, 1H, Ar—H), 7.19 (m, 5H, Ar—H), 6.94 (dd, 1H, Ar—H), 6.82 (d, 1H, Ar—H), 6.46 (d, 2H,

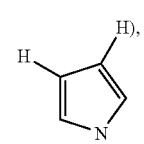

5.93 (d, 2H,

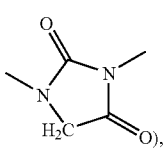

4.28 (s, 2H,

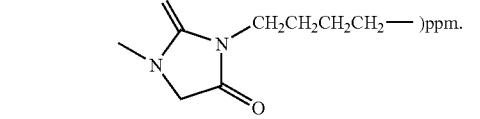

4.23 (t, 2H,

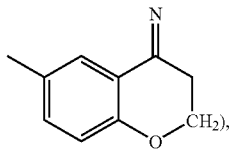

3.92 (t, 2H, —OCH2Ar), 3.55 (t, 2H,

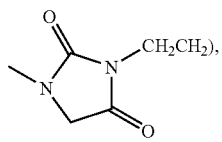

2.92 (t, 2H,

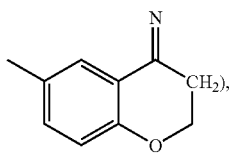

2.74 (t, 2H,

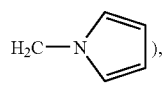

1.72 (m, 4H,

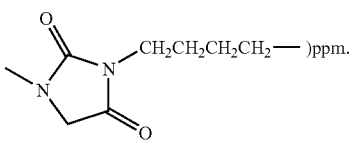)ppm.

Example 26

1-[4-(2,3-dihydro-6-hydroxy)sulfo-benzopyran]imino group-3-(4-(4-(2-hydroxy ethyl)piperazine)-1-yl)butyl-2,4-imidazole dione

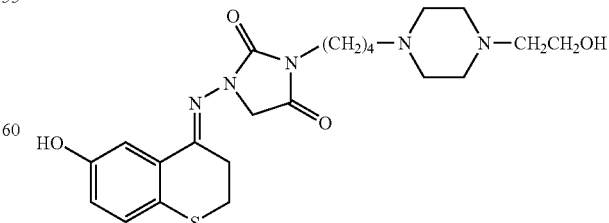

processing as the method in the example 14, except for para-hydrosulphonyl benzamide in place of para hydroxybenzene methyl ether, to prepare 2,3-dihydro-6-hydroxy sulfo-benzopyran 1.2 g. yield: 65.12%; in Step (4), 1-amino-3-[4-(4-ethoxy piperazine) butyl]-2,4-imidazole dione in place of 1-amino-3-[4-(4-methyl-1-piperazine) butyl]-2,4-imidazole dione, to obtain light yellow oil of the title compound 0.56 g, yield: 38.39%.

IR (KBr, cm$^{-1}$): 3556, 2937, 1774, 1713, 1594, 1446, 1413, 1040, 911, 823, 731

EI-MS: m/z 461: M↑$^±$; m/z 98 (Base Peak):

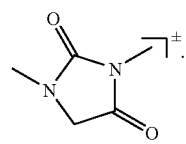

$^1$H-NMR (CDCl$_3$), δ: 7.40 (s, 1H, Ar—H), 6.92 (dd, 1H, Ar—H), 6.77 (d, 1H, Ar—H), 4.5-6.0 (w, 1H, —OH), 4.26 (s, 2H,

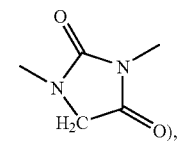

4.20 (t, 2H,

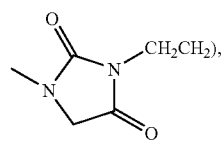

3.63 (t, 2H, N—CH2CH2OH), 3.53 (t, 2H,

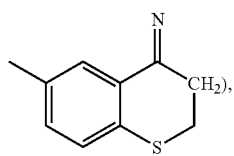

2.90 (t, 2H,

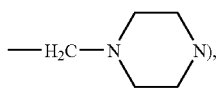

2.71 (t, 2H,

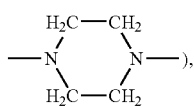

2.55 (t, 2H, N—CH2CH2H), 2.46 (s, 8H,

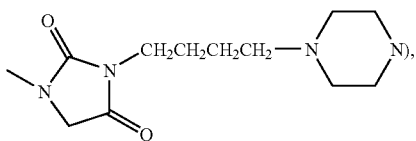

1.64 (m, 2H,

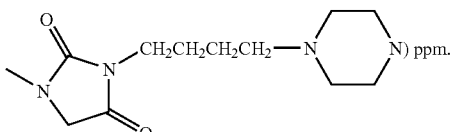

1.60 (s, 2H,

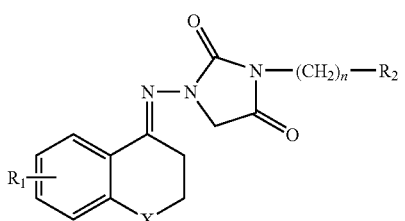 ppm.

What is claimed is:

1. A chroman compound of formula (I) or pharmaceutical salts thereof:

(I)

in which X is O or S; n is 2, 3, or 4; R$_1$ is 6-substituted or 7-substituted halogen, C$_{1-4}$alkyl, C$_{1-4}$alkoxyl, benzyloxyl, carbamoyl; R$_2$ is nitrogen-containing five-membered or six membered heterocyclic ring selected from: piperidinyl, morpholinyl, N-methyl-piperazinyl, N-(2-ethoxyl)-piperazinyl, pyrrolyl, pyrazolyl or imidazolyl.

2. The chroman compound according to claim 1, characterized in that its pharmaceutical salt is a difumarate salt.

3. A method for preparing the chroman compound of formula (I) according to claim 1 comprising the following steps:

(1) R$_1$ substituted phenol as the starting material, reacting with 3-chloropropionic acid in the presence of KOH or NaOH to obtain intermediate compound 3-(R$_1$ substituted phenoxy)propionic acid, in which the R$_1$ is defined as in claim 1;

(2) Dissolving the 3-($R_1$ substituted phenoxy)propionic acid in polyphosphonic acid, stirring, to obtain intermediate compound 2,3-dihydro-6(7)-$R_1$ substituted benzopyran-4-one;

(3) Stirring the 2,3-dihydro-6(7)-$R_1$ substituted benzopyran-4-one in refluxing HBr and glacial acetic acid, to obtain 2,3-dihydro-6(7)-hydroxyl benzopyran-4-one;

(4) Reacting 2,3-dihydro-6(7)-hydroxyl benzopyran-4-one with haloalkyl or haloaryl hydrocarbons in the presence of $K_2CO_3$, $Na_2CO_3$, or $NaHCO_3$ and acetonitrile or acetone, stirring under refluxing to obtain intermediate compound 2,3-dihydro-6(7)-alkoxy-$R_1$ substituted benzopyran-4-one or 2,3-dihydro-6(7)-benzyloxy-$R_1$ substituted benzopyran-4-one;

(5) Reacting 2,3-dihydro-6(7)-substituted benzopyran-4-one with compound (III) in a solvent selected from methanol, ethanol and n-butyl alcohol, adjusting pH to the range of 3-6 by glacial acetic acid, stirring under refluxing to obtain target compound of formula (I); optionally subsequently reacting the target compound of formula (I) with fumaric acid to obtain difumarate of the target compound;

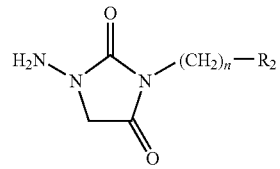

(III)

in which n is 2, 3 or 4; $R_1$ is 6-substituted or 7-substituted halogen, $C_{1-4}$alkyl, $C_{1-4}$alkoxyl, benzyloxyl, carbamoyl; $R_2$ is nitrogen-containing pentatomic or hexahydric substituted heterocyclic ring selected from piperidinyl, morpholinyl, N-methyl-piperazinyl, N-(2-ethoxyl)-piperazinyl, pyrrolyl, pyrazolyl or imidazolyl.

4. A method for treating arrhymia comprising administering to a subject an antiarrhythmic amount of a compound or pharmaceutical salts thereof of claim 1.

5. A pharmaceutical composition comprising a compound of formula (I) according to claim 1 or pharmaceutical salts thereof.

* * * * *